United States Patent
Long et al.

(10) Patent No.: US 11,576,818 B2
(45) Date of Patent: Feb. 14, 2023

(54) NEGATIVE PRESSURE WOUND THERAPY DRESSINGS WITH LOCAL OXYGEN GENERATION FOR TOPICAL WOUND THERAPY AND RELATED METHODS

(71) Applicant: KCI LICENSING, INC., San Antonio, TX (US)

(72) Inventors: Justin Alexander Long, San Antonio, TX (US); Christopher Brian Locke, Blandford Forum (GB); Timothy Mark Robinson, Blandford Forum (GB); Richard Coulthard, San Antonio, TX (US)

( * ) Notice: Subject to any disclaimer, the term of this patent is extended or adjusted under 35 U.S.C. 154(b) by 0 days.

(21) Appl. No.: 16/960,964

(22) PCT Filed: Jan. 4, 2019

(86) PCT No.: PCT/US2019/012273
§ 371 (c)(1),
(2) Date: Jul. 9, 2020

(87) PCT Pub. No.: WO2019/139829
PCT Pub. Date: Jul. 18, 2019

(65) Prior Publication Data
US 2021/0059862 A1  Mar. 4, 2021

Related U.S. Application Data

(60) Provisional application No. 62/615,772, filed on Jan. 10, 2018.

(51) Int. Cl.
*A61F 13/00* (2006.01)
*A61F 13/02* (2006.01)
*A61M 1/00* (2006.01)

(52) U.S. Cl.
CPC .... *A61F 13/00068* (2013.01); *A61F 13/0216* (2013.01); *A61M 1/73* (2021.05);
(Continued)

(58) Field of Classification Search
CPC ............ A61F 13/0216; A61F 13/00068; A61F 2013/00174; A61F 2013/0017;
(Continued)

(56) References Cited

U.S. PATENT DOCUMENTS 5,792,090 A * 8/1998 Ladin ...................... A61L 15/18
424/449
2003/0050674 A1 3/2003 Joshi
(Continued)

FOREIGN PATENT DOCUMENTS

| CN | 205924317 | 2/2017 |
|----|-----------|--------|
| EP | 2956101   | 12/2015 |

(Continued)

OTHER PUBLICATIONS

"What is an Electronic Controller?" Trerice, http://www.cpinc.com/trerice/Control/control_43_44.pdf (Year: 2001).*
(Continued)

*Primary Examiner* — Susan S Su
*Assistant Examiner* — Eric Rassavong

(57) ABSTRACT

This disclosure includes negative pressure wound therapy dressings with local oxygen generation for topical wound therapy. The dressings (18) for facilitating delivery of oxygen and application of negative pressure to target tissue include a manifold (46) that defines a plurality of gas passageways (50) and is configured to allow communication of oxygen to the target tissue; an oxygen-generating material (146) that is configured to release oxygen when exposed to water; a gas-occlusive layer (74) configured to be disposed over the manifold and the oxygen-generating material and
(Continued)

coupled to tissue surrounding the target tissue such that an interior volume containing the manifold and the oxygen-generating material is defined between the gas-occlusive layer and the target tissue; and a port (94) coupled to the gas-occlusive layer and configured to be coupled to a negative pressure source.

20 Claims, 12 Drawing Sheets

(52) U.S. Cl.
CPC .............. *A61M 1/743* (2021.05); *A61M 1/90* (2021.05); *A61M 1/915* (2021.05); *A61M 1/94* (2021.05); *A61M 1/962* (2021.05); *A61M 1/964* (2021.05); *A61M 1/966* (2021.05); *A61F 2013/00174* (2013.01); *A61M 1/95* (2021.05); *A61M 2202/0208* (2013.01)

(58) Field of Classification Search
CPC .......... A61M 1/85; A61M 1/90; A61M 1/743; A61M 2202/0208; A61M 1/74; A61M 1/73; A61M 2205/3324
See application file for complete search history.

(56) References Cited

U.S. PATENT DOCUMENTS

| | | | |
|---|---|---|---|
| 2004/0260253 | A1 | 12/2004 | Rosati |
| 2006/0200100 | A1 | 9/2006 | Rosati |
| 2009/0227969 | A1 | 9/2009 | Jaeb et al. |
| 2009/0259171 | A1 | 10/2009 | Joshi et al. |
| 2010/0069858 | A1 | 3/2010 | Olson |
| 2010/0305490 | A1* | 12/2010 | Coulthard ............. A61M 1/985 604/313 |
| 2011/0034861 | A1* | 2/2011 | Schaefer ................ A61M 1/94 604/23 |
| 2012/0059301 | A1 | 3/2012 | Franklin |
| 2012/0209226 | A1* | 8/2012 | Simmons ............ A61F 13/0246 604/319 |
| 2013/0211318 | A1* | 8/2013 | Croizat ............... A61M 3/0208 604/23 |
| 2016/0030722 | A1* | 2/2016 | Anderson ............. A61M 1/915 604/20 |
| 2016/0166781 | A1 | 6/2016 | Sarangapani et al. |
| 2016/0175500 | A1 | 6/2016 | Cali et al. |
| 2017/0319394 | A1 | 11/2017 | Chen et al. |
| 2019/0030223 | A1* | 1/2019 | Lin ........................ A61M 3/022 |
| 2020/0121510 | A1* | 4/2020 | Hartwell ............. A61F 13/0206 |

FOREIGN PATENT DOCUMENTS

| | | |
|---|---|---|
| TW | 200942281 | 10/2009 |
| TW | M525742 | 7/2016 |
| WO | WO 1996/032082 | 10/1996 |
| WO | WO 2009/066106 | 5/2009 |
| WO | WO 2009/097534 | 8/2009 |
| WO | WO 2009/146441 | 12/2009 |
| WO | WO 2009/158500 | 12/2009 |
| WO | WO 2011/008497 | 1/2011 |
| WO | WO 2011/008711 | 1/2011 |
| WO | WO 2013/066694 | 5/2013 |
| WO | WO 2014/144762 | 9/2014 |
| WO | WO 2015/123353 | 8/2015 |

OTHER PUBLICATIONS

International Search Report and Written Opinion issued in Corresponding PCT Application No. PCT/US2019/012273, dated May 16, 2019.
International Search Report and Written Opinion issued in Corresponding PCT Application No. PCT/US2018/051408, dated Jan. 23, 2019.
International Search Report and Written Opinion issued in Corresponding PCT Application No. PCT/US2018/052137, dated Dec. 19, 2018.
International Search Report and Written Opinion issued in Corresponding PCT Application No. PCT/US2019/012250, dated May 7, 2019.
International Search Report and Written Opinion Issued in Corresponding PCT Patent Application No. PCT/US2018/057214, dated Jan. 31, 2019.

\* cited by examiner

NEGATIVE PRESSURE WOUND THERAPY DRESSINGS WITH LOCAL OXYGEN GENERATION FOR TOPICAL WOUND THERAPY AND RELATED METHODS

CROSS-REFERENCE TO RELATED APPLICATIONS

This application is a national phase application under 35 U.S.C. § 371 of International Application No. PCT/US2019/012273, filed Jan. 4, 2019, which claims priority to and the benefit of U.S. Provisional Application No. 62/615,772, filed Jan. 10, 2018. The contents of the referenced patent applications are incorporated into the present application in their entirety.

BACKGROUND

1. Field of Invention

The present invention relates generally to wound dressings, and more specifically, but not by way of limitation, to negative pressure wound therapy dressings with local oxygen generation for topical wound therapy and related methods.

2. Description of Related Art

Clinical studies and practice have shown that topical applications of therapeutic oxygen can improve wound healing, especially in chronic wounds. Topical applications of therapeutic oxygen can reduce tissue inflammation and/or improve tissue proliferation (e.g., improve collagen synthesis, growth factor production, angiogenesis, and/or the like).

Traditional oxygen-based therapies deliver oxygen with the use of hyperbaric oxygen chambers, oxygen concentrating devices, continuously-diffusing oxygen generating devices, and animal-derived hemoglobin. These traditional oxygen-based therapies offer relatively short treatment periods, reduce patient mobility, and/or require investment in expensive equipment and/or proprietary wound dressings.

While the clinical benefits of topical applications of therapeutic oxygen are known, reductions in the expense and/or improvements to the efficacy, simplicity, and/or mobility of therapy systems, components, and related methods may benefit healthcare providers and patients.

SUMMARY

Some embodiments of the present dressings, which are configured to facilitate delivery of oxygen and application of negative pressure to target tissue, comprise: a manifold that defines a plurality of gas passageways and is configured to allow communication of oxygen to the target tissue; an oxygen-generating material that is configured to release oxygen when exposed to water; a gas-occlusive layer configured to be disposed over the manifold and the oxygen-generating material and coupled to tissue surrounding the target tissue such that: an interior volume containing the manifold and the oxygen-generating material is defined between the gas-occlusive layer and the target tissue; and the gas-occlusive layer limits escape of oxygen from the interior volume between the gas-occlusive layer and the tissue surrounding the target tissue; and a port coupled to the gas-occlusive layer and configured to be coupled to a negative pressure source.

Some embodiments of the present dressings comprise a filter configured to filter fluid that flows through the port. In some embodiments of the present dressings, the filter comprises a layer of material that is bonded to an outer surface or an inner surface of the gas-occlusive layer. In some embodiments of the present dressings, the filter is liquid-occlusive. In some embodiments of the present dressings, the filter comprises polytetrafluoroethylene, a polyester, a polyamide, a copolymer thereof, or a blend thereof.

Some embodiments of the present dressings comprise a negative pressure source configured to be coupled to the port. In some embodiments of the present dressings, the negative pressure source comprises a pump. In some embodiments of the present dressings, the pump comprises a disc pump.

Some embodiments of the present dressings comprise an oxygen-generating portion that includes the oxygen-generating material. In some embodiments of the present dressings, the oxygen-generating portion comprises a water-sorbent material. In some embodiments of the present dressings, the water-sorbent material comprises sodium chloride and/or Bentonite BP. In some embodiments of the present dressings, the oxygen-generating portion comprises a carbon dioxide-sorbent material. In some embodiments of the present dressings, the carbon dioxide-sorbent material comprises sodium carbonate. In some embodiments of the present dressings, the manifold comprises a first manifold layer and a second manifold layer, each defining a plurality of the gas passageways; and the oxygen-generating portion is configured to be disposed between the first and second manifold layers.

Some embodiments of the present dressings comprise a container including a sidewall that defines a chamber; wherein the oxygen-generating portion is disposed within the chamber; and wherein the gas-occlusive layer is configured to be disposed over the container.

In some embodiments of the present dressings, at least a portion of the sidewall is gas-occlusive.

In some embodiments of the present dressings, the gas-occlusive portion of the sidewall comprises polyurethane, polyethylene, polyvinyl acetate, polyvinyl chloride, polyvinylidene chloride, isobutylene, a halogenated isomer, a copolymer thereof, or a blend thereof.

Some embodiments of the present dressings comprise one or more valves coupled to the container and configured to permit fluid communication between the chamber and the interior volume.

Some embodiments of the present dressings, which are configured to facilitate delivery of oxygen and application of negative pressure to target tissue, comprise: a manifold that defines a plurality of gas passageways and is configured to allow communication of oxygen to the target tissue; an oxygen-generating assembly comprising: a container including a sidewall that defines a chamber, at least a portion of the sidewall being gas-occlusive; and an oxygen-generating material disposed within the chamber and configured to release oxygen when exposed to water; and a gas-occlusive layer configured to be disposed over the manifold and the oxygen-generating assembly and coupled to tissue surrounding the target tissue such that: an interior volume containing the manifold and the oxygen-generating assembly is defined between the gas-occlusive layer and the target tissue; and the gas-occlusive layer limits escape of oxygen from the interior volume between the gas-occlusive layer and the tissue surrounding the target tissue; wherein the oxygen-generating assembly includes one or more valves configured to permit fluid communication between the chamber and the interior volume.

Some embodiments of the present dressings comprise a port coupled to the gas-occlusive layer and configured to be coupled to a negative pressure source. Some embodiments of the present dressings comprise a filter configured to filter fluid that flows through the port. In some embodiments of the present dressings, the filter comprises a layer of material that is bonded to an outer surface or an inner surface of the gas-occlusive layer. In some embodiments of the present dressings, the filter is liquid-occlusive. In some embodiments of the present dressings, the filter comprises polytetrafluoroethylene, a polyester, a polyamide, a copolymer thereof, or a blend thereof. Some embodiments of the present dressings comprise a negative pressure source configured to be coupled to the port. In some embodiments of the present dressings, the negative pressure source comprises a pump. In some embodiments of the present dressings, the pump comprises a disc pump.

In some embodiments of the present dressings, the oxygen-generating assembly comprises a water-sorbent material disposed within the chamber. In some embodiments of the present dressings, the water-sorbent material comprises sodium chloride and/or Bentonite BP.

In some embodiments of the present dressings, the oxygen-generating assembly comprises a carbon dioxide-sorbent material. In some embodiments of the present dressings, the carbon dioxide-sorbent material comprises sodium carbonate.

In some embodiments of the present dressings, the gas-occlusive portion of the sidewall comprises polyurethane, polyethylene, polyvinyl acetate, polyvinyl chloride, polyvinylidene chloride, isobutylene, a halogenated isomer, a copolymer thereof, or a blend thereof.

In some embodiments of the present dressings, the manifold comprises a first manifold layer and a second manifold layer, each defining a plurality of the gas passageways; and the oxygen-generating assembly is configured to be disposed between the first and second manifold layers. In some embodiments of the present dressings, at least one of the one or more valves is configured to relieve pressure within the chamber when pressure within the chamber meets or exceeds a threshold pressure. In some embodiments of the present dressings, at least one of the one or more valves comprises a one-way valve configured to: permit fluid communication out of the chamber through the valve; and prevent fluid communication into the chamber through the valve. In some embodiments of the present dressings, at least one of the one or more valves comprises a thin film valve. In some embodiments of the present dressings, at least one of the one or more valves comprises a solenoid valve. In some embodiments of the present dressings, at least one of the one or more valves is movable between: a first position; and a second position in which fluid communication between the chamber and the interior volume through the valve is more restricted than when the valve is in the first position. In some embodiments of the present dressings, at least one of the one or more valves is configured to move toward the second position if pressure within the interior volume meets or falls below a threshold pressure. In some embodiments of the present dressings, at least one of the one or more valves is configured to move toward the first position if pressure within the chamber rises above or at least a threshold value above pressure within the interior volume. In some embodiments of the present dressings, at least one of the one or more valves is configured to move toward the first position if pressure within the chamber meets or rises above a threshold pressure. Some embodiments of the present dressings comprise a controller configured to move at least one of the one or more valves between the first and second positions.

Some embodiments of the present dressings comprise one or more sensors configured to capture data indicative of pressure within the interior volume; wherein the controller is configured to move at least one of the one or more valves between the first and second positions based, at least in part, on data captured by the one or more sensors. In some embodiments of the present dressings, the controller is configured to move at least one of the one or more valves toward the second position if pressure within the interior volume, as indicated in data captured by at least one of the one or more sensors, meets or falls below a threshold pressure. In some embodiments of the present dressings, the controller is configured to control the negative pressure source based, at least in part, on data captured by the one or more sensors. In some embodiments of the present dressings, the controller is configured to deactivate the negative pressure source if pressure within the interior volume, as indicated in data captured by at least one of the one or more sensors, meets or falls below a threshold pressure. In some embodiments of the present dressings, the controller is configured to activate the negative pressure source to reduce pressure within the interior volume if pressure within the interior volume, as indicated in data captured by at least one of the one or more sensors, meets or rises above a threshold pressure. In some embodiments of the present dressings, the controller is configured to move at least one of the one or more valves toward the second position upon or after activation of the negative pressure source. In some embodiments of the present dressings, the controller is configured to move at least one of the one or more valves toward the first position upon or after deactivation of the negative pressure source. In some embodiments of the present dressings, the controller comprises a processor.

In some embodiments of the present dressings, the oxygen-generating material comprises an adduct of hydrogen peroxide. In some embodiments of the present dressings, the adduct of hydrogen peroxide comprises sodium percarbonate and/or hydrogen peroxide-urea.

Some embodiments of the present dressings comprise a liquid control layer having a plurality of perforations, the liquid control layer configured to be disposed beneath the oxygen-generating material and to restrict communication of exudate toward the target tissue. In some embodiments of the present dressings, the liquid control layer comprises a film.

Some embodiments of the present dressings comprising a patient-interface layer configured to be disposed in contact with the tissue surrounding the target tissue, the patient interface layer defining a plurality of openings configured to allow communication of oxygen and exudate through the patient-interface layer. In some embodiments of the present dressings, the patient-interface layer comprises a polymer, optionally, silicone, polyethylene, ethylene vinyl acetate, a copolymer thereof, or a blend thereof. In some embodiments of the present dressings, the patient-interface layer includes an adhesive configured to couple the patient-interface layer to the tissue surrounding the target tissue.

In some embodiments of the present dressings, the manifold comprises a foam or a non-woven textile. In some embodiments of the present dressings, the manifold comprises polyethylene, a polyolefin, a polyether, polyurethane, a co-polyester, a copolymer thereof, or a blend thereof.

In some embodiments of the present dressings, the gas-occlusive layer comprises a film. In some embodiments of the present dressings, the gas-occlusive layer has a thickness that is between approximately 15 micrometers (μm) and approximately 40 μm. In some embodiments of the present dressings, the gas-occlusive layer comprises polyurethane, polyethylene, polyvinyl acetate, polyvinyl chloride, polyvinylidene chloride, isobutylene, a halogenated isomer, a copolymer thereof, or a blend thereof. In some embodiments of the present dressings, the gas-occlusive layer includes an adhesive configured to couple the gas-occlusive layer to the tissue surrounding the target tissue. Some embodiments of the present dressings comprises a valve coupled to the gas-occlusive layer and configured to relieve pressure within the interior volume when pressure within the interior volume meets or exceeds a threshold pressure. In some embodiments of the present dressings, the valve comprises a one-way valve configured to: permit fluid communication out of the interior volume through the valve; and prevent fluid communication into the interior volume through the valve. In some embodiments of the present dressings, the valve comprises a thin film valve or a check valve.

Some embodiments of the present dressings comprise a sensor configured to detect a presence of oxygen within the interior volume. In some embodiments of the present dressings, the sensor comprises a material configured to be disposed within the interior volume and to change color in response to a change in oxygen concentration within the interior volume. In some embodiments of the present dressings, the material comprises a pressure-sensitive paint. In some embodiments of the present dressings, the material comprises a redox indicator. In some embodiments of the present dressings, the redox indicator comprises methylene blue, phenosafranine, indigo carmine, resazurin, N-phenylanthranilic acid, and/or neutral red. In some embodiments of the present dressings, the material is disposed on an inner surface of the gas-occlusive layer. In some embodiments of the present dressings, the sensor comprises: a layered silicate; a cationic surfactant; an organic colorant; and a reducing agent.

Some embodiments of the present dressings comprise a sensor configured to detect a pH of fluid within the interior volume. In some embodiments of the present dressings, the sensor comprises a material configured to be disposed within the interior volume and to change color in response to a change in pH of fluid within the interior volume. In some embodiments of the present dressings, the material is configured to absorb carbon dioxide. In some embodiments of the present dressings, the material is configured to absorb ammonia. In some embodiments of the present dressings, the material is disposed on an inner surface of the gas-occlusive layer.

Some embodiments of the present systems comprise any of the present dressings; and a source of fluid configured to be coupled to the dressing such that fluid communication between the source of fluid and the oxygen-generating material is permitted.

Some embodiments of the present methods comprise coupling any of the present dressings to a patient's tissue; and reducing pressure within the interior volume. Some embodiments of the present methods for delivering oxygen and applying negative pressure to target tissue comprise coupling a dressing comprising a manifold that defines a plurality of gas passageways, an oxygen-generating material that is configured to release oxygen when exposed to water, and a gas-occlusive layer to a patient's tissue such that the gas-occlusive layer is disposed over the manifold and the oxygen-generating material and is coupled to tissue surrounding the target tissue such that: an interior volume containing the manifold and the oxygen-generating material is defined between the gas-occlusive layer and the target tissue; and the gas-occlusive layer limits escape of oxygen from the interior volume between the gas-occlusive layer and the tissue surrounding the target tissue; and reducing pressure within the interior volume. In some embodiments of the present methods, reducing pressure within the interior volume is performed using a negative pressure source that is in fluid communication with the interior volume.

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any disclosed embodiment, the term "substantially" may be substituted with "within [a percentage] of" what is specified, where the percentage includes 0.1, 1, 5, and 10 percent.

The phrase "and/or" means and or. The phrase "and/or" includes any and all combinations of one or more of the associated listed items. To illustrate, A, B, and/or C includes: A alone, B alone, C alone, a combination of A and B, a combination of A and C, a combination of B and C, or a combination of A, B, and C. In other words, "and/or" operates as an inclusive or.

The terms "comprise" (and any form of comprise, such as "comprises" and "comprising"), "have" (and any form of have, such as "has" and "having"), and "include" (and any form of include, such as "includes" and "including") are open-ended linking verbs. As a result, an apparatus that "comprises," "has," or "includes" one or more elements possesses those one or more elements, but is not limited to possessing only those elements. Likewise, a method that "comprises," "has," or "includes," one or more steps possesses those one or more steps, but is not limited to possessing only those one or more steps.

Any embodiment of any of the apparatuses, systems, and methods can consist of or consist essentially of—rather than comprise/have/include—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The feature or features of one embodiment may be applied to other embodiments, even though not described or illustrated, unless expressly prohibited by this disclosure or the nature of the embodiments.

Further, an apparatus that is configured in a certain way is configured in at least that way, but it can also be configured in other ways than those specifically described.

Some details associated with the embodiments are described above, and others are described below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure.

Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures. Figures having schematic views are not drawn to scale.

DETAILED DESCRIPTION

Figure 1:
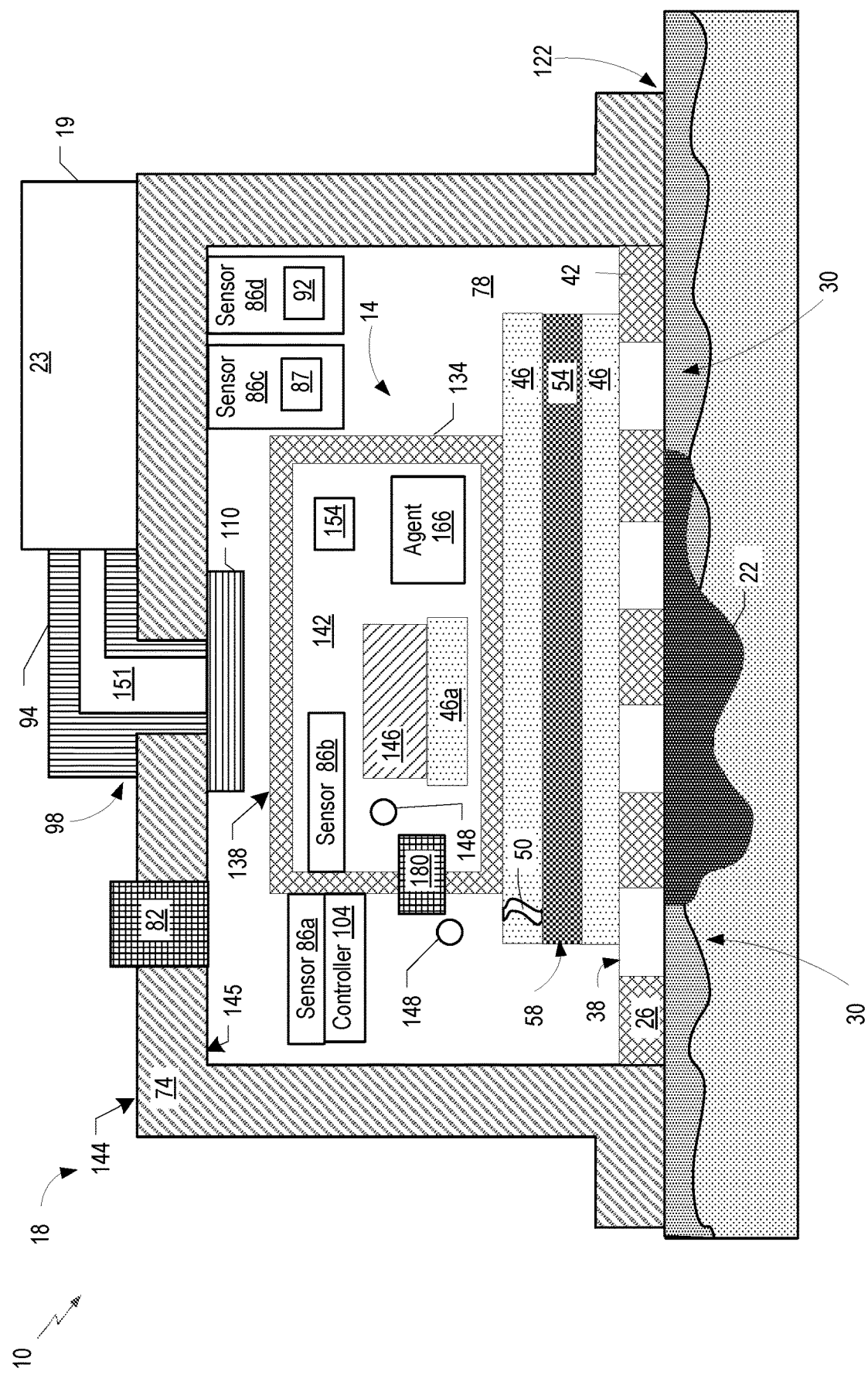
FIG. 1 is a cross-sectional schematic view of an embodiment of the present systems.

Referring to FIG. 1, shown therein and designated by the reference numeral 10 is one embodiment of the present systems for providing topical wound therapy. System 10 includes a wound dressing 18 configured to be coupled to target tissue 22 and/or to tissue 30 surrounding the target tissue to facilitate delivery of oxygen and application of negative pressure to the target tissue.

The term "target tissue" as used herein can broadly refer to a wound (e.g., open or closed), a tissue disorder, and/or the like located on or within tissue, such as, for example, bone tissue, adipose tissue, muscle tissue, neural tissue, dermal tissue, vascular tissue, connective tissue, cartilage, tendons, ligaments, and/or the like. The term "target tissue" as used herein can also refer to areas of tissue that are not necessarily wounded or exhibit a disorder, but include tissue that would benefit from tissue generation. The term "wound" as used herein can refer to a chronic, subacute, acute, traumatic, and/or dehisced incision, laceration, puncture, avulsion, and/or the like, a partial-thickness and/or full thickness burn, an ulcer (e.g., diabetic, pressure, venous, and/or the like), flap, and/or graft.

System 10 can include a negative pressure source 23. Negative pressure source 23 can be coupled to dressing via a conduit. Negative pressure source 23 can be configured to provide negative pressure within an interior volume (e.g., 78) of dressing 18 such that the volume of the interior volume is reduced and/or negative pressure is applied to target tissue 22 and/or tissue 30 surrounding the target tissue to improve wound healing and/or sealing between the dressing and tissue surrounding the target tissue. As used herein, "negative pressure" can refer to a pressure that is less than a local ambient pressure, such as less than atmospheric pressure. Negative pressure source 23 can comprise a mechanically and/or electrically-powered device such as, for example, a disc pump (e.g., a disc micro-pump comprising a dual acting pump capable of providing the intended negative pressures and flows but at noise levels almost undetectable to the human ear), a vacuum pump, a suction pump, a wall suction port, and/or the like. For example, negative pressure source 23 can comprise a housing 19 having a controller configured to physically and/or wirelessly communicate with dressing 18 to receive operating instructions, provide feedback to and/or control other devices, and/or the like. Further, housing 19 can comprise a portable power source configured to provide electrical power to negative pressure source 23. Housing 19 may comprise a soft flexible material to protect the patient and the enclosed electronics.

Figure 2:
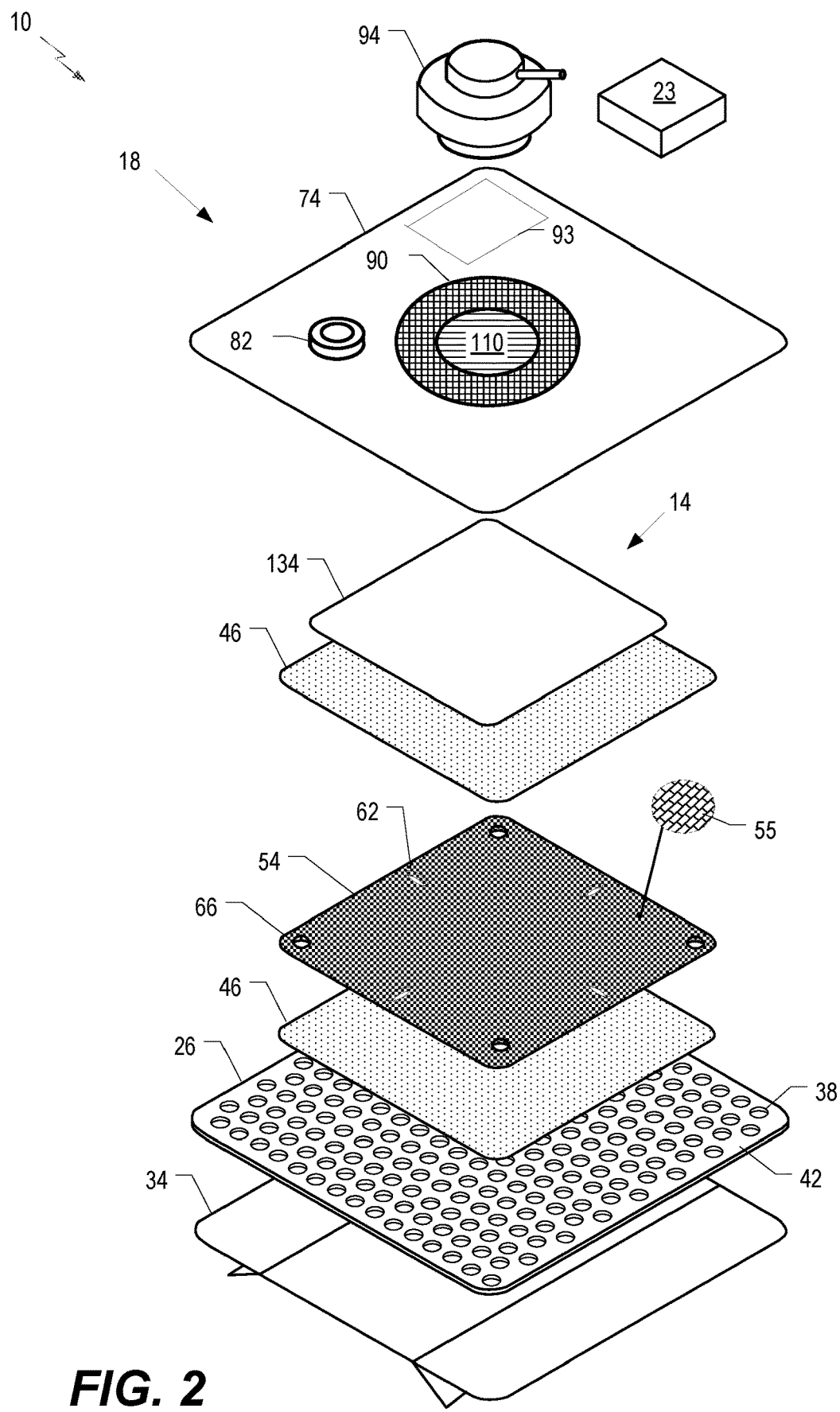
FIG. 2 is an exploded perspective view of a first embodiment of the present wound dressings, suitable for use in some embodiments of the present systems.

As shown in FIGS. 1 and 2, dressing 18 can include a patient-interface layer 26 configured to be in contact with target tissue 22 and/or tissue 30 surrounding the target tissue. For example, patient-interface layer 26 may be disposed over target tissue 22 and be in contact with tissue 30 surrounding the target tissue. For further example, patient-interface layer 26 may be disposed over target tissue 22 such that the patient-interface layer fills at least a portion of a recess defined by the target tissue. Patient-interface layer 26 can comprise any suitable planform shape, planform area, thickness, and/or the like that is appropriate to treat target tissue 22.

Patient-interface layer 26 can comprise an adhesive configured to couple the patient-interface layer to target tissue 22 and/or tissue 30 surrounding the target tissue. Such an adhesive can be configured to have low tack properties to minimize patient discomfort and/or tissue trauma as a result of the application, repositioning, and/or removal of patient-interface layer 26 from target tissue 22 and/or tissue 30 surrounding the target tissue. Such an adhesive may comprise any suitable adhesive, such as, for example, an acrylic adhesive, polyurethane gel adhesive, silicone adhesive, hydrogel adhesive, hydrocolloid adhesive, a combination thereof, and/or the like. For example, such an adhesive may be disposed about the edges of a tissue-facing surface of patient-interface layer 26 (i.e., in an arrangement referred to as a "window pane"). Dressing 18 may include a protective liner 34 configured to be disposed on a surface of patient-interface layer 26 such that the protective liner at least partially covers the adhesive (e.g., prior to application of the dressing onto tissue).

Patient-interface layer 26 can comprise a plurality of openings 38 configured to allow communication of therapeutic gas and exudate through the patient-interface layer and/or to promote granulation of target tissue 22. Each of openings 38 of patient-interface layer 26 can have a circular shape. Openings 38 of patient-interface layer 26 can comprise any suitable shape, such as, for example, circular, elliptical, or otherwise round, square, rectangular, hexagonal, or otherwise polygonal. Each of openings 38 of patient-interface layer 26 may be substantially equal in size (e.g., as measured by a maximum transverse dimension of the opening), such as, for example, approximately any one of, or between approximately any two of, the following: 0.1, 0.2, 0.3, 0.4, 0.5, 0.75, 1.0, 1.25, and 1.5 centimeters (cm). In some embodiments, a patient-interface layer (e.g., 26) may comprise openings (e.g., 38) having different sizes.

Patient-interface layer 26 can comprise a plurality of gas passageways 42 defined by any suitable material, such as, for example, an open-cell foam (e.g., reticulated foam). Each gas passageway 42 can comprise a maximum transverse dimension of 400 and 600 micrometers. Patient-interface layer 26 can be hydrophilic. For example, patient-interface layer 26 can be configured to wick away (e.g., by capillary flow through gas passageways 42) exudate from target tissue 22 and/or tissue 30 surrounding the target tissue.

Patient-interface layer 26 can comprise any suitable material, such as, for example, a polymer, optionally, silicone, a hydrogel, polyvinyl alcohol, polyethylene, a polyurethane, polyether, ethylene vinyl acetate, a copolymer thereof, or a blend thereof. In some embodiments, a patient-interface layer (e.g., 26) can serve as or include a scaffold to promote tissue generation. Such a scaffold may comprise any suitable scaffold for soft tissue healing, such as, for example, autograft tissue, collagen, polylactic acid (PLA), polyglycolic acid (PGA), and/or the like. In some embodiments, a patient-interface layer (e.g., 26) may comprise a biodegradable material, such as, for example, PLA, PGA, a polycarbonate, polypropylene fumarate, polycaprolactone, a polymeric blend thereof, and/or the like.

Non-limiting examples of patient-interface layer 26 include Silbione® HC2 products, which are commercially available from Bluestar Silicones International, of Lyon, France, Nanova™ Dressing Perforated Silicone Wound Contact Layers, which are commercially available from Kinetic Concepts, Inc., of San Antonio, Tex., USA, and Bioflex® Performance Materials, which are commercially available from Scapa Healthcare of Windsor, Conn., USA.

Dressing 18 can include one or more manifolds 46 (i.e., a manifold layer). Each manifold 46 can be configured to allow communication of therapeutic gas (e.g., oxygen 148) to target tissue 22 and/or allow communication of exudate to a sorbent material (e.g., 58) (as discussed in further detail below). For example, each manifold 46 can define a plurality of gas passageways 50 to distribute therapeutic gas across the manifold and/or to collect exudate from target tissue 22 across the manifold. Plurality of gas passageways 50 of each manifold 46 can be interconnected to improve distribution and/or collection of fluids across the manifold. For example, gas passageways 50 can be defined by an open-cell foam (e.g., reticulated foam), tissue paper, gauze, a non-woven textile (e.g., felt), and/or the like. In embodiments where manifold 46 comprises a non-woven textile, dressing 18 can comprise two or more manifolds 46 (e.g., one or more on opposing sides of sorbent layer 54). Manifold 46 can be configured to produce and/or transmit significant apposition forces onto target tissue 22 and/or tissue 30 surrounding the target tissue via mechanical properties and/or due to the presence of certain prescribable defects formed via laser and/or die-cut processes into the bulk of the material of the manifold.

Manifold 46 can comprise any suitable material, such as, for example, polyethylene, a polyolefin, a polyether, polyurethane, a co-polyester, a copolymer thereof, or a blend thereof. For example, in embodiments where manifold 46 comprises a foam, such a foam may be polyether-based polyurethane foam. Manifold 46 can comprise any suitable planform shape, planform area, thickness, and/or the like that is appropriate to treat target tissue 22. In embodiments where manifold 46 comprises a non-woven textile, such a non-woven textile can comprise a density ranging from approximately 80 to 150 grams per square meter (GSM) and a thickness ranging from approximately 2 millimeters (mm) to 12 mm. In embodiments where manifold 46 comprises a foam, such a foam can comprise a porosity ranging from approximately 20 to 120 parts per million (ppm), such as, for example, 45 ppm, and a thickness ranging from approximately 2 mm to 12 mm, such as, for example, 6 mm.

Non-limiting examples of manifold 46 include MEDISPONGE® Foams, which are commercially available from Essentra PLC of Milton Keynes, England, and Exudate Management Systems, which are commercially available from TWE Group GmbH, of Emsdetten, Germany.

Dressing 18 can include a sorbent layer 54. As shown, patient-interface layer 26 can be configured to be disposed below sorbent layer 54 relative to target tissue 22. Sorbent layer 54 can include a sorbent material 58 configured to draw exudate away from target tissue 22 and/or tissue 30 surrounding the target tissue. Sorbent material 58 can be disposed below or above one of manifolds 46 to capture exudate. As shown, sorbent material 58 can be disposed between a first one of manifolds 46 and a second one of the manifolds. Sorbent layer 54, and, more particularly, sorbent material 58, can comprise any suitable adsorbent or absorbent material. Sorbent layer 54 having absorbent material may comprise a hydrophilic material. Suitable examples of an absorbent material (e.g., a material that tends to swell, by 50 percent or more, due to the binding of liquid within the material) includes a foam, a non-woven textile, a superabsorbent polymer, and/or the like. For example, sorbent material 58 having absorbent material may comprise sodium carboxymethyl cellulose (NaCMC) fiber, alginate fiber, and/or the like. Suitable examples of an adsorbent material (e.g., a material that has a surface onto which liquid binds such that the material does not swell) include carbon filters, such as, for example, an activated charcoal filter and/or the like. Such an activated charcoal filter can be configured to remove nitrogen from air within an interior volume (e.g., 78) of dressing 18, thereby increasing the purity of oxygen within the interior volume.

Non-limiting examples of sorbent material 58 include superabsorbent wound care laminates having a density of 300 grams per square meter (GSM), which are commercially available from Gelok International of Dunbridge, Ohio, USA, and Absorflex™, which has a density of 800 GSM and is commercially available from Texsus S.p.A. of Chiesina Uzzanese, Italy.

As shown in FIG. 2, sorbent layer 54 can comprise a plurality of perforations 62 and/or a plurality of openings 66, one or more of which are configured to allow fluid communication through the sorbent layer, for example, in instances where sorbent material 58 exhibits gel-blocking. Gel-blocking can occur when sorbent material 58 forms a gel in response to absorption of liquid. Gel-blocking can cause sorbent material 58 to block liquid and/or gas flow through the sorbent material. As shown in FIG. 2, sorbent layer 54 can comprise a textured surface having a plurality of grooves 55 configured to distribute liquid into and/or around sorbent material 58.

In this embodiment, each opening 66 may define an aperture comprising a perimeter that does not substantially change (e.g., does not change by more than 5 percent) in response to fluid flow through the opening. Each perforation 62 may define an aperture comprising a perimeter that substantially changes (e.g., changes by more than 5 percent) in response to fluid flow through the perforation. For example, one or more of perforations 62 may be defined by a slit in sorbent layer 54. Each of openings 66 of sorbent layer 54 may be substantially equal in size (e.g., as measured by a maximum transverse dimension of the opening), such as, for example, approximately any one of, or between approximately any two of, the following: 0.5, 0.75, 1.0, 1.25, and 1.5 cm. Each of perforations 62 of sorbent layer 54 may comprise a size (e.g., as measured by a maximum transverse dimension of the perforation) that is substantially smaller than the size of one or more of openings 66, such as, for example, 50, 60, 70, 80, or 90 percent smaller in size.

Sorbent layer 54 can comprise any suitable planform shape, planform area, thickness, and/or the like appropriate to treat target tissue 22. For example, a planform area of sorbent layer 54 can be smaller than a planform area of one or more manifolds 46 such that, when sorbent layer 54 is disposed between manifolds 46 (i.e., when a manifold is disposed on opposing sides of the sorbent layer), the opposing manifolds can be coupled around a peripheral edge of the sorbent layer to define a pocket. For example, the planform area of sorbent layer 54 can be at least 5 percent smaller, such as, for example, 5, 10, 15, 20, 25, 30, 35, 40, or 45 percent smaller than the planform area of one or more manifolds 46. In this way and others, therapeutic gas can circumvent sorbent layer 54 around its periphery and be distributed from a manifold 46 on a first side of the sorbent layer to a manifold 46 on an opposing second side of the sorbent layer.

Dressing 18 can include a gas-occlusive layer 74. Gas-occlusive layer 74 can be configured to be disposed over one or more manifolds 46 and coupled to tissue 30 surrounding target tissue 22 such that an interior volume 78 containing the manifold(s) is defined between the gas-occlusive layer and the target tissue and such that the gas-occlusive layer limits the escape of therapeutic gas and/or exudate from the interior volume between the gas-occlusive layer and the tissue surrounding the target tissue. Gas-occlusive layer 74 can limit escape of therapeutic gas (e.g., oxygen 148) between the gas-occlusive layer and tissue 30 surrounding target tissue 22 such that, by providing therapeutic gas to dressing 18 at one or more of the volumetric flow rates and/or oxygen concentrations described herein, system 10 can attain an oxygen concentration of at least 80 percent (e.g., 80, 85, 90, 92, 94, 96, 98 or more percent) within interior volume 78 of the dressing within a time duration of approximately 4 to 8 hours (e.g., approximately any one of, or between approximately any two of: 4, 4.5, 5, 5.5, 6, 6.5, 7, 7.5, and 8 hours).

As shown, gas-occlusive layer 74 can be configured to be disposed over sorbent layer 54 such that interior volume 78 contains the sorbent material. In other words, sorbent layer 54, and thus, sorbent material 58, can be configured to be disposed below gas-occlusive layer 74. A portion of gas-occlusive layer 74 can be coupled to tissue 30 surrounding target tissue 22 via patient-interface layer 26. To illustrate, a tissue-facing surface of gas-occlusive layer 74 can comprise an adhesive, such as, for example, an acrylic adhesive, polyurethane gel adhesive, silicone adhesive, a combination thereof, and/or the like, configured to couple the gas-occlusive layer to patient-interface layer 26 and/or tissue 30 surrounding target tissue 22. For example, when gas-occlusive layer 74 is coupled to patient-interface layer 26, such an adhesive may flow through one or more of openings 38 of the patient-interface layer to adhere gas-occlusive layer 74 to tissue 30 surrounding target tissue 22.

Gas-occlusive layer 74 can be sterile such that the gas-occlusive layer provides a viral and/or bacterial barrier to target tissue 22. Gas-occlusive layer 74 can be configured to provide a layer of protection from physical trauma to target tissue 22. In some embodiments, a portion of a gas-occlusive layer (e.g., 74) may be configured to be gas-permeable to provide a suitable (e.g., moist) wound healing environment and/or to prevent passive permeation of therapeutic gas molecules through the gas-occlusive layer. Gas-occlusive layer 74 can comprise an oxygen permeability coefficient ($P \times 10^{10}$), at 25 degrees Celsius, ranging from 0.0003 to 0.5 (e.g., approximately any one of, or between approximately any two of the following: 0.0003, 0.0004, 0.0005, 0.0006, 0.0007, 0.0008, 0.0009, 0.001, 0.005, 0.01, 0.05, 0.1, 0.15, 0.2, 0.25, 0.3, 0.35, 0.4, 0.45, and 0.5), where P is measured in units of $[(cm^3)(cm)]/[(cm^2)(s)(cm\ Hg)]$ which represents [(amount of permeate)(gas-occlusive layer thickness)]/[(surface area)(time)(pressure-drop across the gas-occlusive layer)]. Gas-occlusive layer 74 can comprise a moisture vapor transmission rate (MVTR) of at least 250 grams per meters squared per day ($g/m^2/day$). In embodiments where a tissue-facing surface of gas-occlusive layer 74 comprises an adhesive (as discussed above), the adhesive may affect the gas permeability and/or the MVTR of the gas-occlusive layer. To illustrate, for a gas-occlusive layer (e.g., 74) having a film with a thickness of 0.025 mm and an adhesive with a thickness of 0.025 mm, the gas permeability and MVTR of the gas-occlusive layer are half as much as the gas permeability and MVTR of the same gas-occlusive layer without the adhesive.

Gas-occlusive layer 74 may comprise a flexible film, such as, for example, a hydrocolloid sheet. Gas-occlusive layer 74 can comprise any suitable material that limits escape of therapeutic gas and/or exudate through the gas-occlusive layer, such as, for example, polyurethane, polyethylene, polyvinyl acetate, polyvinyl chloride, polyvinylidene chloride, isobutylene, a halogenated isomer (e.g., chlorobutyl and/or bromobutyl), epichlorohydrin, a copolymer thereof, or a blend thereof. Gas-occlusive layer 74 can comprise any suitable planform shape, planform area, thickness, and/or the like that is appropriate to treat target tissue 22. For example, gas-occlusive layer 74 can comprise a thickness that is approximately any one of, or between approximately any two of the following: 5, 10, 15, 20, 25, 30, 35, 40, 45, 50, 55, and 60 micrometers.

Referring again to FIG. 1, system 10 comprises oxygen-generating device 14. As shown, oxygen-generating device 14 may be disposed between manifold 46 and gas-occlusive layer 74. In some embodiments, oxygen-generating device 14 may be disposed between one or more manifolds 46 and sorbent layer 54.

Oxygen-generating device 14 includes a container 134 that is disposed within interior volume 78 of dressing 18. Container 134 can comprise any suitable storage device, such as, for example, a canister, pouch, sachet, bag, box, and/or the like.

Container 134 comprises a sidewall 138 that defines a chamber 142 configured to be in fluid communication with interior volume 78 of dressing 18 (e.g., via a valve 180). At least a portion of sidewall 138 of container 134 can be rigid or flexible, can be gas-occlusive, or a combination thereof. Sidewall 138 can be substantially similar to gas-occlusive layer 74. Sidewall 138 can comprise any suitable material that limits escape of oxygen and/or exudate through the sidewall, such as, for example, comprising polyurethane, polyethylene, polyvinyl acetate, polyvinyl chloride, polyvinylidene chloride, isobutylene, a halogenated isomer, a copolymer thereof, or a blend thereof.

System 10 comprises an oxygen-generating material 146 disposed within chamber 142 of container 134. Oxygen-generating material 146 is configured to release oxygen 148 (e.g., a gas whose composition is approximately 99 or more percent oxygen) when exposed to water. Water, in this context, includes any substance having $H_2O$, such as, for example, liquid water, water vapor, and/or other substances that include water, such as, for example, exudate from target tissue 22. Oxygen-generating material 146 can comprise an adduct of hydrogen peroxide, such as, for example, sodium percarbonate and/or hydrogen peroxide-urea.

Liquid source 150 can comprise one or more capsules configured to be disposed within chamber 142 of container 134. Each of the capsules can define a pocket that can include water. In this embodiment, flexion and/or breakage of a portion of at least one of the capsules can cause the capsule to release water from within the pocket. The capsules can comprise any suitable material, such as, for example, polyethylene, polyether, polyurethane, a co-polyester, a co-polymer, a blend thereof, or a foil film or laminate.

Container 134 may comprise a manifold 46a, which is substantially similar to manifold 46 of dressing 18. Manifold 46a can be disposed within chamber 142 of container 134. Oxygen-generating material 146 can be disposed above or below and coupled to manifold 46. For example, oxygen-generating material 146 can be coupled to manifold 46a by an adhesive. Manifold 46a can be configured to distribute and/or expose water to oxygen-generating material 146.

System 10 can be configured to regulate the amount of water exposed to oxygen-generating material, thereby preventing oversaturation of the oxygen-generating material and limiting the rate and/or volume of oxygen emission. For example, system 10 can comprise a competitive agent 166 disposed within chamber 142 of container 134 and configured to limit the communication of oxygen between the chamber of the container and interior volume 78 of dressing 18. Competitive agent 166 can comprise any suitable material that absorbs water, such as, for example, sodium carbonate, bentonite, and/or the like. In some embodiments, a competitive agent (e.g., 166) comprises an adhesive that bonds an oxygen-generating material (e.g., 146) to a manifold (e.g., 46a). In some embodiments, a competitive agent (e.g., 166) comprises a sorbent material, which is substantially similar to sorbent material 58 and is configured to capture water within a chamber (e.g., 142) of a container (e.g., 134). In some embodiments, a competitive agent (e.g., 166) comprises one or more valves within a container (e.g., 134) configured to provide water a tortuous flow path before being exposed to an oxygen-generating material (e.g., 146).

In some embodiments, a chamber (e.g., 142) of a container (e.g., 134) can comprise two or more sub-chambers (e.g., separated by a physical barrier, such as, for example, a weld, an adhesive, and/or the like), each comprising a discrete volume of an oxygen-generating material (e.g., 146) and/or a competitive agent (e.g., 166). Each of such sub-chambers can be exposed to water in sequence such that the oxygen-generating material (e.g., 146) within such a chamber (e.g., 142) is reacted in phases, rather than at once.

Dressing 18 may comprise one or more valves 180 coupled to container 134 to regulate the amount and/or rate of oxygen exposed to target tissue 22. Valve(s) 180 may be configured to permit fluid communication between chamber 142 and interior volume 78. More particularly, valve 180 comprises a one-way valve configured to permit fluid communication out of chamber 142 through the valve and to prevent fluid communication into the chamber through the valve. Valve(s) 180 can comprise any suitable one-way valve, such as, for example, a ball-check valve, a thin film valve, a diaphragm check valve, and/or the like.

Valve(s) 180 may be configured to relieve pressure within chamber 142 when pressure within the chamber meets or exceeds a threshold pressure. Valve(s) 180 can be movable between a first position and a second position in which fluid communication between chamber 142 and interior volume 78 through the valve(s) is more restricted than when the valve(s) are in the first position. In a particular implementation, the first position corresponds to an open position and the second position corresponds to a closed position.

In some embodiments, valve(s) 180 may be pneumatically actuated. For example, when pressure within chamber 142 is less than or equal to a threshold pressure, valve(s) 180 are configured to move towards the second position. When pressure within the chamber 142 is equal to or greater than a threshold value, valve(s) 180 are configured to move towards the first position. For further example, valve(s) 180 can be configured to move towards the first position when the pressure within chamber 142 is equal to or greater than a threshold amount above the pressure with interior volume 78. In this way and others, when negative pressure is applied within interior volume 78 (e.g., via negative pressure source 23), valve(s) 180 move towards the second position, thereby restricting or blocking oxygen flow from chamber 142 to the interior volume, and when negative pressure is not applied within the interior volume, the valve(s) move towards the second position, thereby permitting oxygen flow from the chamber to the interior volume.

Dressing 18 can comprise a valve 82 coupled to gas-occlusive layer 74. Valve 82 can be configured to permit communication of gas out of interior volume 78 through the valve and prevent communication of gas into the interior volume through the valve. For example, valve 82 can be configured to relieve pressure within interior volume 78 when the pressure within the interior volume exceeds a threshold pressure. Such a threshold pressure may range from 8 to 24 mmHg (e.g., approximately any one of, or between approximately any two of the following: 8, 10, 12, 14, 16, 18, 20, 22, and 24 mmHg). Valve 82 can comprise any suitable one-way valve, such as, for example, a ball-check valve, a thin film valve, a diaphragm check valve, and/or the like. In this way and others, valve 82 can be configured to ensure that interior volume 78 does not become over-pressurized with therapeutic gas such that dressing 18 and tissue 30 surrounding target tissue 22 separate to allow therapeutic gas therebetween.

Dressing 18 may comprise one or more sensors, such as sensors 86a-86d, configured to collect data indicative of the presence, volume, and/or concentration of therapeutic gas (e.g., oxygen) and/or liquid (e.g., exudate) within interior volume 78 and/or the pressure within interior volume 78. Sensors (e.g., 86a-86d) may operate passively (i.e., the sensor may not require an external power source). Sensor 86a is disposed in interior volume 78, such as outside chamber 142, and is configured to detect data indicative of pressure within interior volume 78. Sensor 86b is disposed within chamber 142 and is configured to detect data indicative of pressure within the chamber.

Sensor 86c is configured to detect data indicative of the oxygen purity of air within interior volume 78. Sensor 86c can comprise a material 87 configured to be disposed within interior volume 78. For example, material 87 of sensor 86c can be disposed on a lower (i.e., tissue-facing) surface of gas-occlusive layer 74. Material 87 can be configured to change color in response to a change in concentration of therapeutic gas within the interior volume. For example, material 87 of sensor 86c can comprise a pressure-sensitive paint, a redox indicator (e.g., comprising methylene blue, phenosafranine, indigo carmine, resazurin, N-phenylanthranilic acid, and/or neutral red). In some embodiments, a sensor (e.g., 86c) can comprise a layered silicate, a cationic surfactant, an organic colorant, and a reducing agent. For example, in embodiments where material 87 comprises an organic colorant, the colorant can be configured to exhibit a first color when the material is exposed to oxygen having a concentration that is less than or equal to 20 percent. Such an organic colorant can be configured to begin gradually changing color from the first color to a second color when the concentration of oxygen within interior volume 78 becomes equal to or greater than approximately 20 percent. Such an organic colorant can be configured to continue gradually changing color from the first color to the second color until the concentration of oxygen within interior volume 78 is approximately 90 to 95 percent, at which time the colorant exhibits only the second color. In some embodiments where material 87 comprises an organic colorant, the colorant can change to a plurality of colors graduated in scale, each signifying a different oxygen concentration within interior volume (e.g., a pink color when the oxygen concentration is approximately 20 percent, a red color when it is approximately percent 40, a purple color when it is approximately 60 percent, and a blue color when it is approximately 80 percent).

As shown in FIG. 2, sensor 86c may be coupled to a display 90 configured to indicate, such as, for example, via a color change, the presence, volume, and/or concentration of oxygen within interior volume 78. A non-limiting example of sensor 86c includes the Ageless Eye™ Oxygen Indicator, which is commercially available from Mitsubishi Gas Chemical Company, Inc., of Tokyo, Japan, that is modified to change color in response to oxygen exceeding 20 percent purity.

Dressing 18 may comprise a sensor 86d configured to detect a pH of fluid within interior volume 78. Sensor 91 can comprise a material 92 configured to be disposed within interior volume 78. Similar to material 87, material 92 can be configured to be disposed on a lower (e.g., tissue-facing) surface of gas-occlusive layer 74.

Material 92 can be configured to change color in response to a change in pH of fluid (e.g., liquid, such as, for example, exudate) within the interior volume. For example, material 92 of sensor 91 can be configured to absorb carbon dioxide and/or ammonia. In some embodiments, material 92 comprises litmus paper. Like sensor 86c, sensor 86d may be coupled to a display 93 configured to indicate, such as, for example, via a color change, a change in pH of fluid within interior volume 78. While sensors 86a, 86c, and 86d are described as distinct sensors, in some embodiments, sensors 86a, 86c, and 86d may be the same sensor.

Controller 104 (e.g., a processor) is configured to move at least one of valve(s) 180 between the first position (e.g., an open position) and the second position (e.g., a closed position). For example, controller 104 may move valve(s) 180 between the first and second positions based, at least in part, on data collected by and received from sensor(s) 86a-86d. To illustrate, controller 104 is configured to move at least one of valve(s) 180 toward the second position (e.g., the closed position) when pressure within interior volume 78, as indicated by data collected by and received from sensor 86a, is less than or equal to a threshold pressure. In some embodiments, controller 104 may be configured to control valve 82 when pressure within interior volume 78, as indicated by data collected by and received from sensor 86a, exceeds a threshold pressure such that the valve relieves pressure within the interior volume to ensure the dressing is not over pressurized.

As shown, controller 104 can be located within interior volume 78. In such an implementation, controller 104 may be electrically coupled to one or more components that are located within and/or located outside of interior volume 78. Controller 104 may be coupled to an outer surface 144 or an inner surface 145 of gas occlusive layer 74. Controller 104 can be electronically coupled to one or more components within interior volume 78, such as one or more of sensors 86a-86d or valve(s) 180. To illustrate, a connector (e.g., an electrical communication terminal) may be coupled to outer surface 144 and/or incorporated in gas occlusive layer 74. The connector may be electrically coupled one or more components within interior volume 78, such as one or more of sensors 86a-86d or valve(s) 180, and may be configured to be removably coupled to at least controller 104.

Controller 104 can be configured to be wired and/or wirelessly coupled to negative pressure source 23. For example, controller 104 may be configured to control negative pressure source 23 based, at least in part, on data captured by one or more sensors 86a-86d. To illustrate, controller 104 may be configured to deactivate the negative pressure source 23 when pressure within interior volume 78, as indicated by data captured by sensor 86a, is less than or equal to a threshold pressure. Conversely, controller 104 may be configured to activate negative pressure source 23 to reduce pressure within interior volume 78 when pressure within the interior volume, as indicated by data captured by sensor 86a, is equal to or greater than the threshold pressure. Controller 104 can be configured to move valve(s) 180 toward the second position upon or after activation of negative pressure source 23. Conversely, controller 104 can be configured to move valve(s) 180 toward the first position upon or after deactivation of negative pressure source 23. Controller 104 may determine, based on data captured by sensor(s) 86a and 86b, a pressure value, such as an instantaneous pressure within interior volume 78 and/or chamber 142, an average pressure within the interior volume and/or the chamber during a time period, a rate of pressure change within the interior volume and/or the chamber, and/or the like.

Gas-occlusive layer 74 can comprise one or more openings 98 configured to allow the application of negative pressure into interior volume 78 of dressing 18. For example, opening 98 of gas-occlusive layer 74 can be configured to receive a port 94.

Dressing 18 may comprise one or more ports 94, each of which are configured to be coupled to a respective opening 98 of gas-occlusive layer 74 or defined by the gas-occlusive layer. Port 94 can include a channel 151 and can be configured to allow fluid communication between negative pressure source 23 and interior volume 78. Port 94 can comprise a filter (e.g., substantially similar to filter 110, as described below) such that the filter filters fluid that flows through the port.

Port 94 can be releasably coupled to negative pressure source 23 and/or dressing 18 such that the negative pressure source can be decoupled from the dressing without removing the dressing from target tissue 22 and/or tissue 30 surrounding the target tissue. Port 94 may comprise an adhesive configured to seal around opening 98 of gas-occlusive layer 74 in order to minimize the diffusion of air between the port and the gas-occlusive layer.

A non-limiting example of port 94 includes the T.R.A.C.™ Pad, which is commercially available from Kinetic Concepts, Inc., of San Antonio, Tex., USA.

In this embodiment, dressing 18 comprises a filter 110 configured to filter fluid that flows through opening 98 of gas-occlusive layer 74. For example, filter 110 can be sterile such that the filter provides a viral and/or bacterial barrier. As shown, filter 110 comprises a layer of material that is bonded to inner surface 145 of gas-occlusive layer 74. In some embodiments, a filter (e.g., 110) comprises a layer of material that is bonded to an outer surface 144 of a gas-occlusive layer (e.g., 74). Filter 110 can comprise any suitable material, such as, for example, polytetrafluoroethylene (PTFE) (e.g., an expanded PTFE), a polyester, a polyamide, polyolefin, a copolymer thereof, a blend thereof, and/or the like. Filter 110 can have a backing material, such as, for example, a non-woven textile, comprising a polyester, a polyamide, and/or the like. Filter 110 may comprise a hydrophobic material. To illustrate, filter 110 can be configured to allow communication of gas between interior volume 78 and negative pressure source 23 to reduce pressure within the interior volume and restrict communication of exudate out of the interior volume through the opening of the gas-occlusive layer. Filter 110 can comprise a pore size of approximately 0.05 to 0.15 micrometers (e.g., approximately any one of or between any two of the following: 0.05, 0.07, 0.09, 0.10, 0.11, 0.13, and 0.15 micrometers).

A non-limiting example of filter 110 includes GORE® Microfiltration Media for Medical Devices, which is commercially available from W. L. Gore & Associates, Inc., of Newark, De., USA.

Figure 3:
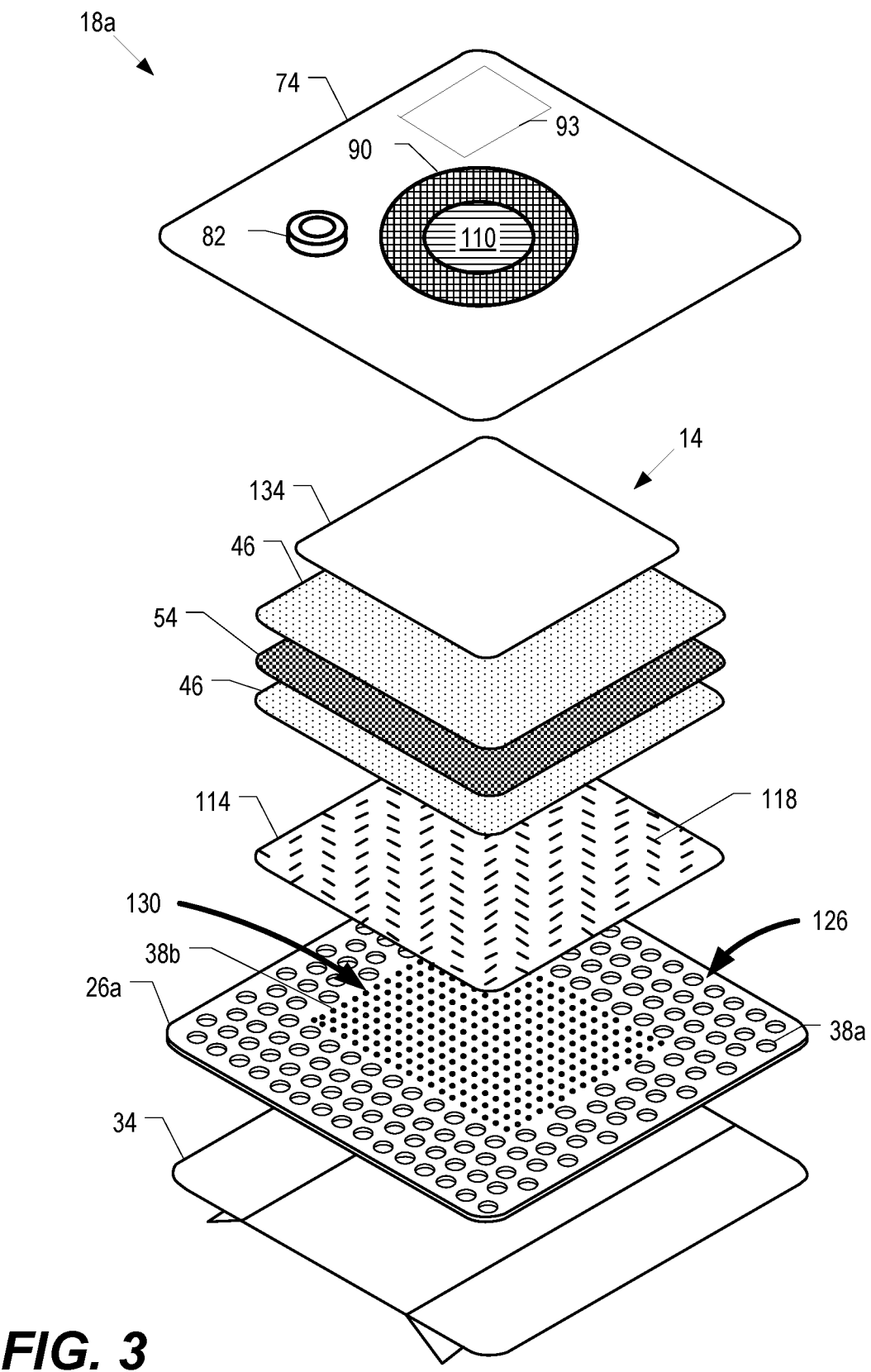
FIG. 3 is an exploded perspective view of a second embodiment of the present wound dressings, suitable for use in some embodiments of the present systems.

Referring now to FIG. 3, shown therein and designated by the reference numeral 18a is another embodiment of the present wound dressings for facilitating delivery of oxygen and application of negative pressure to target tissue 22. Dressing 18a is substantially similar to dressing 18, with the primary exception that dressing 18a comprises a liquid control layer 114 configured to restrict communication of exudate toward the target tissue.

As shown in FIG. 3, liquid control layer 114 can be configured to be disposed below one or more manifolds 46 (e.g., between the manifold(s) and target tissue 22). Sorbent layer 54, and thus, sorbent material 58, can be disposed between one or more manifolds 46 and liquid control layer 114 to capture exudate. In other words, liquid control layer 114 can be configured to be disposed below sorbent layer 54, and thus, below sorbent material 58. In some embodiments, a liquid control layer (e.g., 114) can be disposed between a manifold (e.g., 46) and a sorbent layer (e.g., 54).

Liquid control layer 114 can comprise a plurality of perforations 118 configured to permit exudate to flow away from target tissue 22 through the plurality of perforations and block the flow of exudate toward the target tissue through the plurality of perforations. Each perforation 118 may define an aperture comprising a perimeter that changes (e.g., changes by more than 5 percent) in response to fluid flow through the perforation. Each of perforations 118 of liquid control layer 114 may be substantially equal in size (e.g., as measured by a maximum transverse dimension of the opening), such as, for example, approximately any one of, or between approximately any two of, the following: 1, 2, 3, 4, or 5 millimeters (mm). For example, one or more of plurality of perforations 118 may comprise a slit. One or more perforations 118 can be configured to allow fluid communication through liquid control layer 114 and to prevent gel-blocking in sorbent material 58.

Liquid control layer 114 can comprise any suitable material to restrict communication of exudate toward target tissue 22. For example, liquid control layer 114 can comprise a foam, a non-woven textile, and/or a film. For further example, liquid control layer 114 can comprise a hydrophilic material, such as, for example, a superabsorbent polymer.

Dressing 18a includes a patient-interface layer 26a, which is substantially similar to patient-interface layer 26 with the exception that patient-interface layer 26a comprises a first portion 126 comprising a first plurality openings 38a, each having a first size (e.g., as measured by a maximum transverse dimension of the first opening, examples of which are provided above in relation to openings 38), and a second portion 130 comprising a second plurality of openings 38b, each having a second size (e.g., as measured by a maximum transverse dimension of the second opening) that is at least 50 percent (e.g., 50, 55, 65, 70, 75, 80, 85, 90, or 95 or more percent) smaller than the first size. For example, each of second plurality of openings 38b may be substantially equal in size (e.g., as measured by a maximum transverse dimension of the opening), such as, for example, approximately any one of, or between approximately any two of, the following: 0.1, 0.2, 0.3, 0.4, and 0.5 cm.

In this embodiment, respective ones of second plurality of openings 38b of patient-interface layer 26a and respective ones of plurality of perforations 118 of liquid control layer 114 may be misaligned relative to each other to define a tortuous path for exudate tending to backflow toward target tissue 22, thereby frustrating the backflow of the exudate toward the target tissue. As shown in FIG. 3, patient-interface layer 26a can be configured to be disposed below liquid control layer 114. In some embodiments, a patient-interface layer (e.g., 26a) can be omitted and a liquid control layer (e.g., 114) can be disposed directly onto target tissue (e.g., 22).

Some embodiments of the present methods comprise: coupling a dressing (e.g., 18, 18a) to a patient's tissue (e.g., 22 and/or 30); and reducing pressure within the interior volume (e.g., 78).

Some embodiments of a method for delivering oxygen and applying negative pressure to target tissue (e.g., 22) comprise: coupling a dressing (e.g., 18, 18a) comprising a manifold (e.g., 46) that defines a plurality of gas passageways (e.g., 50), an oxygen-generating material (e.g., 146) that is configured to release oxygen when exposed to water, and a gas-occlusive layer (e.g., 74) to a patient's tissue (e.g., 22 and/or 30) such that the gas-occlusive layer is disposed over the manifold and the oxygen-generating material and is coupled to tissue surrounding the target tissue such that: an interior volume (e.g., 78) containing the manifold and the oxygen-generating material is defined between the gas-occlusive layer and the target tissue; and the gas-occlusive layer limits escape of oxygen from the interior volume between the gas-occlusive layer and the tissue surrounding the target tissue; and reducing pressure within the interior volume.

In some embodiments of the present methods, reducing pressure within the interior volume is performed using a negative pressure source (e.g., 23) that is in fluid communication with the interior volume.

EXAMPLES

The present invention will be described in greater detail by way of specific examples. The following examples are offered for illustrative purposes only and are not intended to limit the invention in any manner. Those of skill in the art will readily recognize a variety of noncritical parameters that can be changed or modified to yield essentially the same results.

Example 1

The Effects of Negative Pressure Wound Therapy and Topical Oxygen Therapy within a Dressing of the Present Disclosure It was discovered that the benefits of negative pressure wound therapy (NPWT) (e.g., apposition forces applied to target tissue (e.g., 22), micro-strain applied to the target tissue, exudate removal from the target tissue, and/or the like) can be delivered concurrently with the benefits of topical oxygen therapy (e.g., providing an increased "feeding" of target tissue 22 cells, improved collagen formation, and/or the like) when pressure within an interior volume (e.g., 78) is maintained such that the partial pressure of oxygen within the target tissue is favorable in a system (e.g., 10) that has a high purity of oxygen, such as greater than 80 percent.

Figure 4:
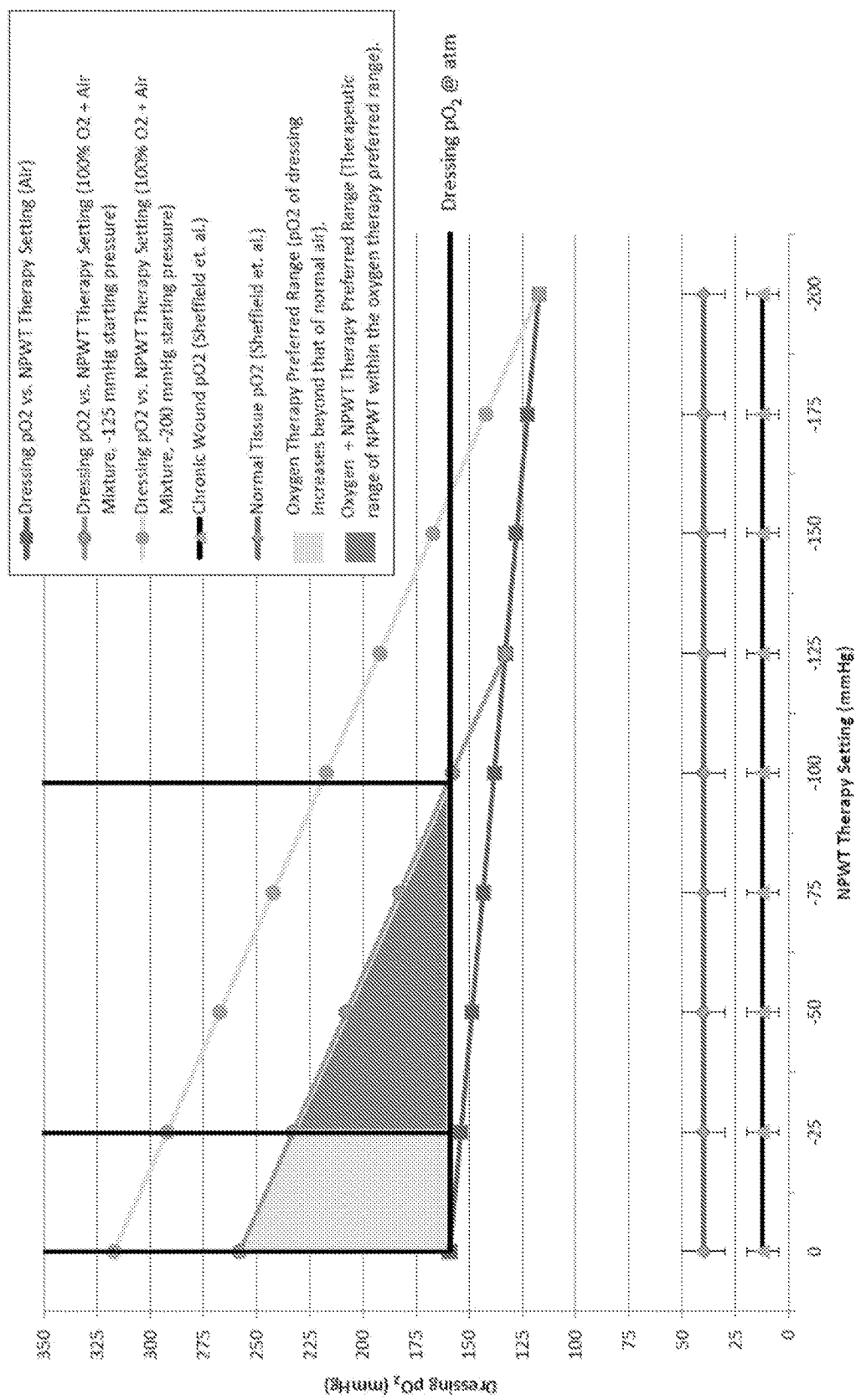
FIGS. 4-12 depict test data of the present dressings based on an application of oxygen and negative pressure within the dressings.

As shown in FIG. 4, the application of NPWT decreased the local partial pressure of oxygen within target tissue (e.g., 22) (see line with square plot points). The resulting partial pressure within target tissue (e.g., 22), after the infusion of 100 percent pure oxygen from starting pressures of −125 and −200 mmHg is represented by the dark gray line with circular plot points and the light gray line with circular plot points, respectively. The combination of the horizontal black line, which represents the partial pressure of oxygen in normal air at atmospheric pressure, and both the dark gray line with circular plot points and the light gray line with circular plot points, each of which represent an infusion of 100 percent pure oxygen at different starting negative pressures, defines two different triangular zones of preferred therapy settings: one for each starting negative pressure (e.g., −125 mmHg and −200 mmHg).

The light gray shaded zone (e.g., defined between 0 mmHg NPWT setting, −25 mmHg NPWT setting, the dark gray line with circular plot points, and the horizontal black line) represents NPWT settings where an infusion of 100 percent pure oxygen into the interior volume (e.g., 78) increased the gradient partial pressure of oxygen between the target tissue (e.g., 22) and the surrounding wound environment (e.g., 30) beyond that of the partial pressure of oxygen at atmospheric pressure. The dark gray shaded zone (e.g., defined between −25 mmHg NPWT setting, the dark gray line with circular plot points, and the horizontal black line) represents the preferred range for NPWT settings where both the influx of 100 percent pure oxygen increased the gradient partial pressure of oxygen between the target tissue (e.g., 22) and the surrounding wound environment (e.g., 30) beyond that of the partial pressure of oxygen at atmospheric pressure and NPWT has a therapeutic benefit when starting at −125 mmHg.

Example 2

Changes in Gas Characteristics of a Dressing During Application of Negative Pressure Wound Therapy A 26 cm by 15 cm by 3 cm V.A.C.® GranuFoam™ Dressing, which is commercially available from Kinetic Concepts, Inc., of San Antonio, Tex., USA, was used to test the required volume to achieve multiple negative pressure levels within an interior volume (e.g., 78) of the dressing. The dressing included, in the following order, from farthest to closest to tissue (e.g., 22 or 30): one T.R.A.C. pad, one adhesive drape (e.g., 74) and a polyurethane foam (e.g., 46) dressing.

For the discussion below, the target negative pressure level, after application of oxygen within the interior volume (e.g., 78), was between −25 mmHg and −100 mmHg.

Figure 5:
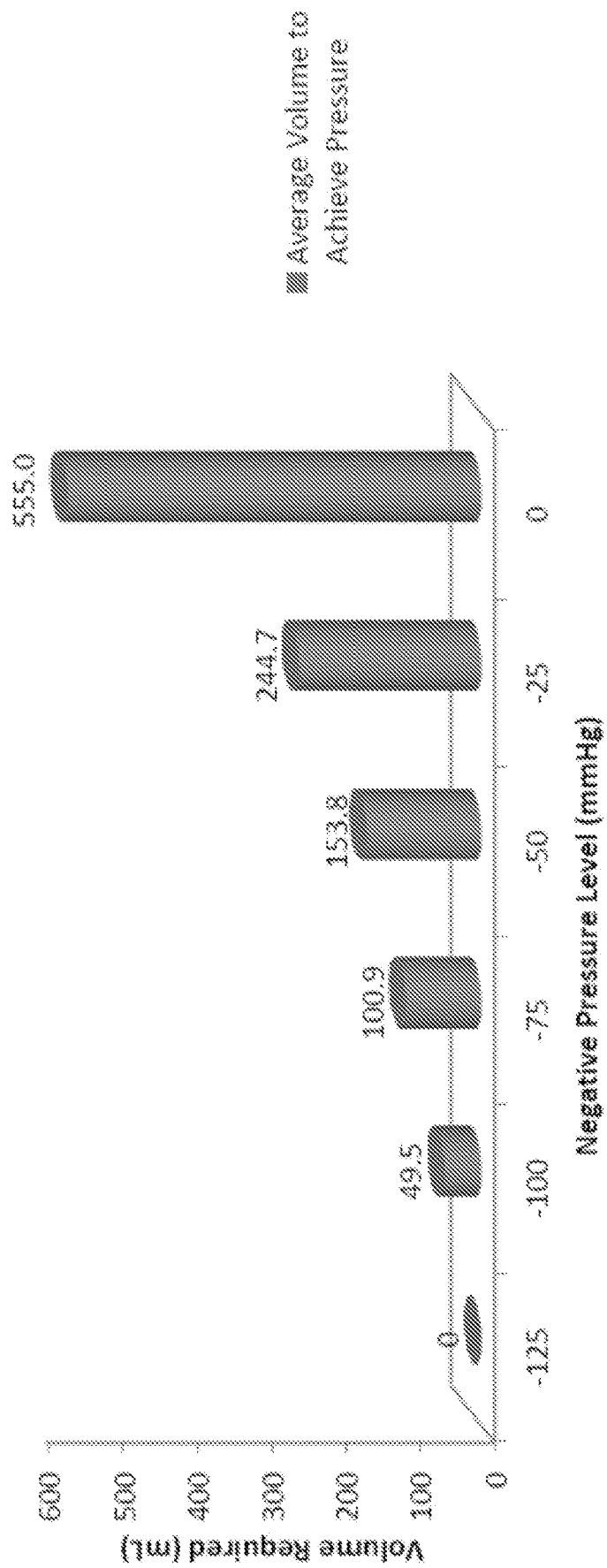

FIG. 5 depicts the volume of oxygen within the interior volume (e.g., 78) of the dressing that is required to achieve certain negative pressure levels within the interior volume.

As shown, a greater volume of oxygen was required to decrease the negative pressure within the interior volume (e.g., 78).

Figure 6:
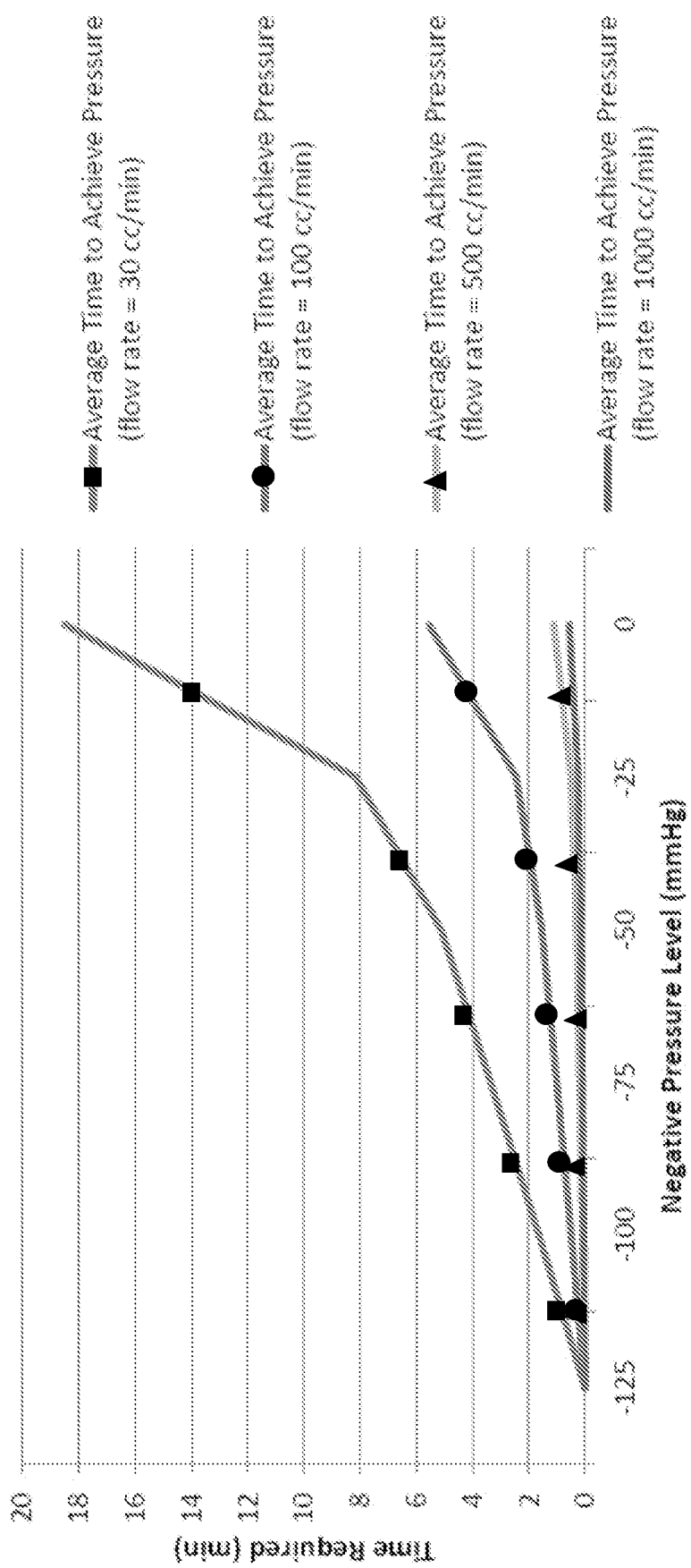

FIG. 6 depicts the duration of time required to achieve certain negative pressure levels within the interior volume (e.g., 78) of the dressing, depending on the volumetric flow rate of oxygen into the interior volume. As shown, a greater flow rate of oxygen was required to decrease the negative pressure within the interior volume (e.g., 78) faster.

Figure 7:
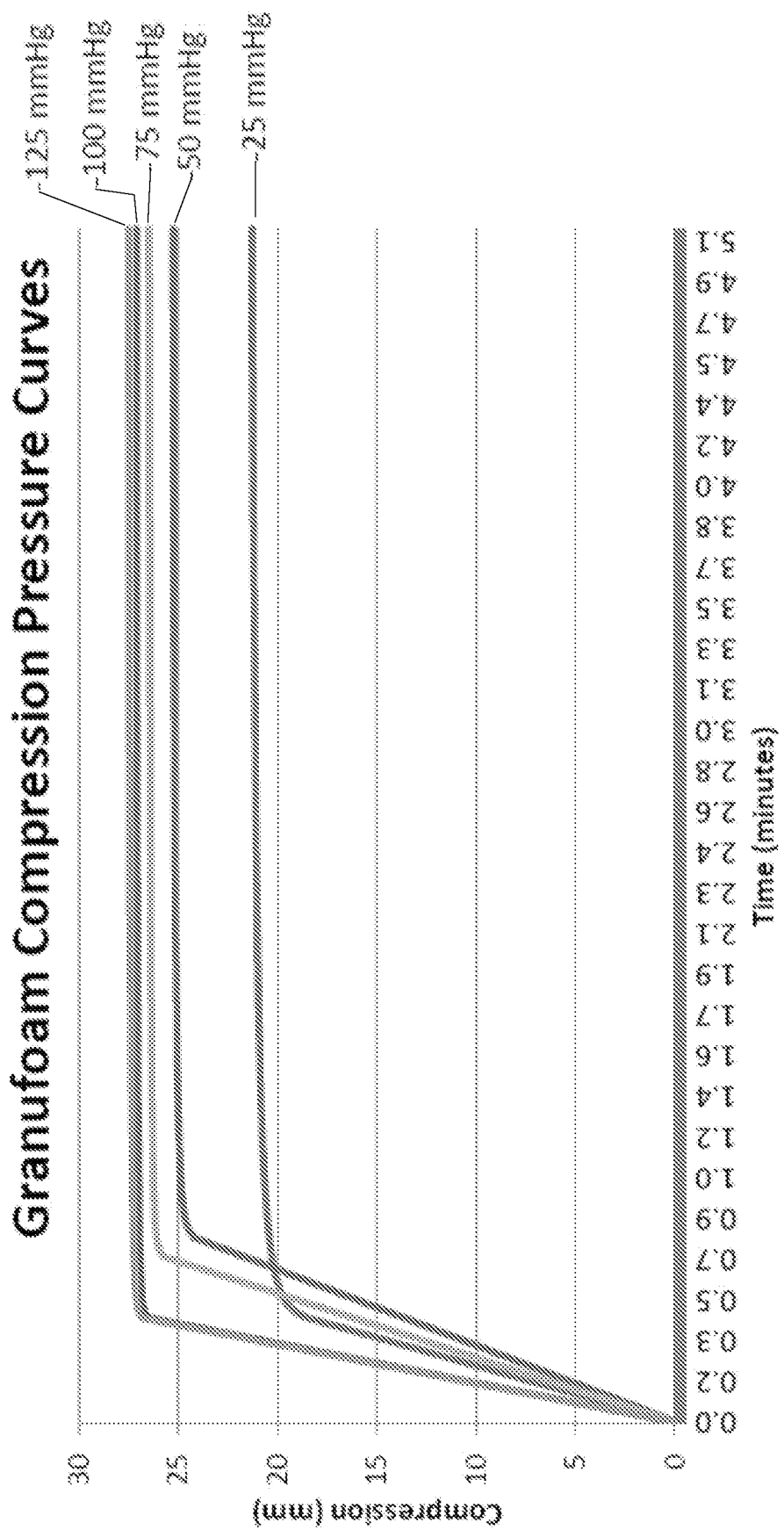

FIG. 7 depicts the change in compression of the polyurethane foam based on certain negative pressures over time. A materials tester, which is commercially available from AMETEK, Inc., of Berwyn, Pa., USA, was used to test the compression of the polyurethane foam. As shown, the duration of time to reach a compression greater than 20 mm was between 0.3 and 0.6 minutes, at negative pressures between −25 mmHg and −125 mmHg.

Figure 8:
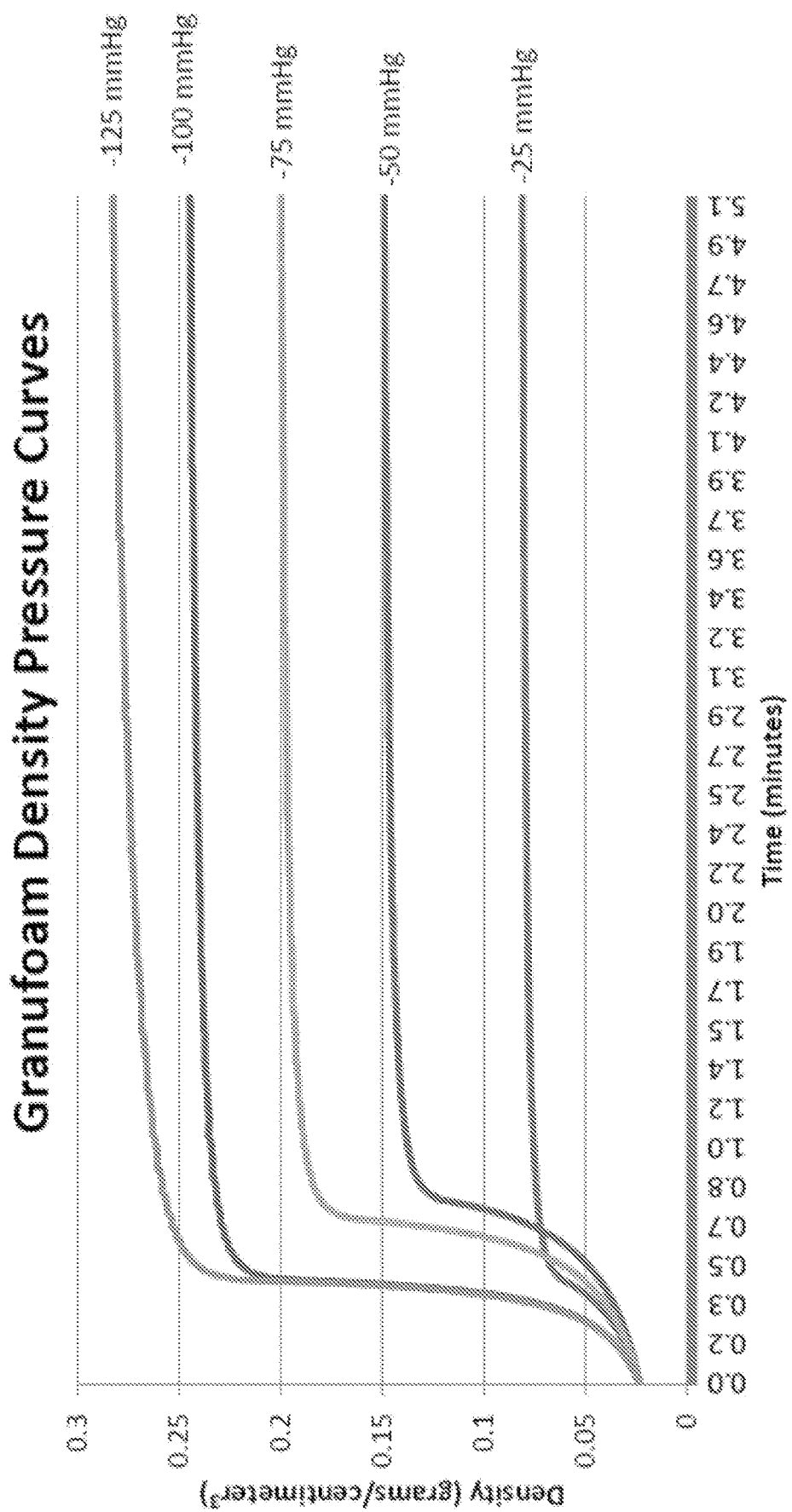
Figure 9:
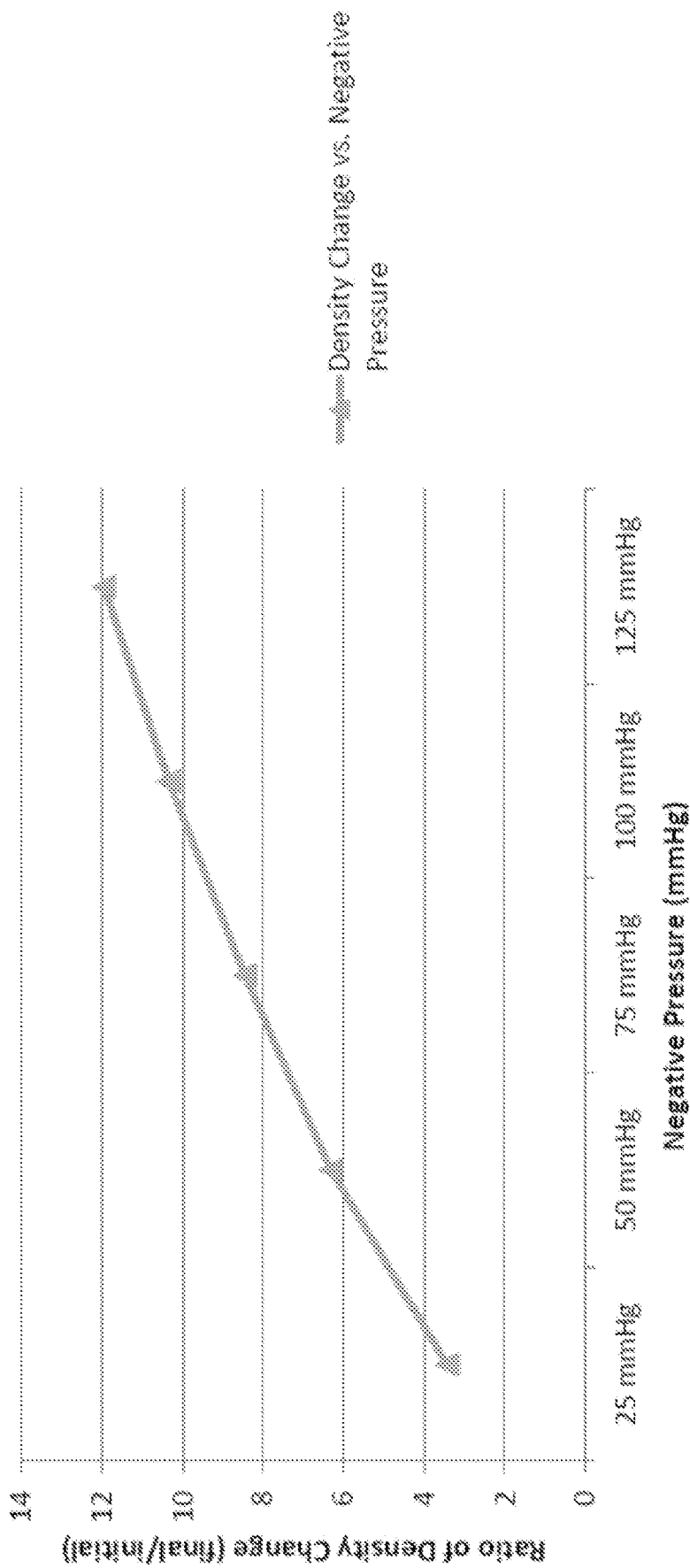

FIG. 8 depicts the change in density of the polyurethane foam based on certain negative pressures over time. A materials tester, which is commercially available from AMETEK, Inc., of Berwyn, Pa., USA, was used to test the density of the polyurethane foam. As shown in FIG. 9, the ratio of density change increased as negative pressure increased.

Figure 10:
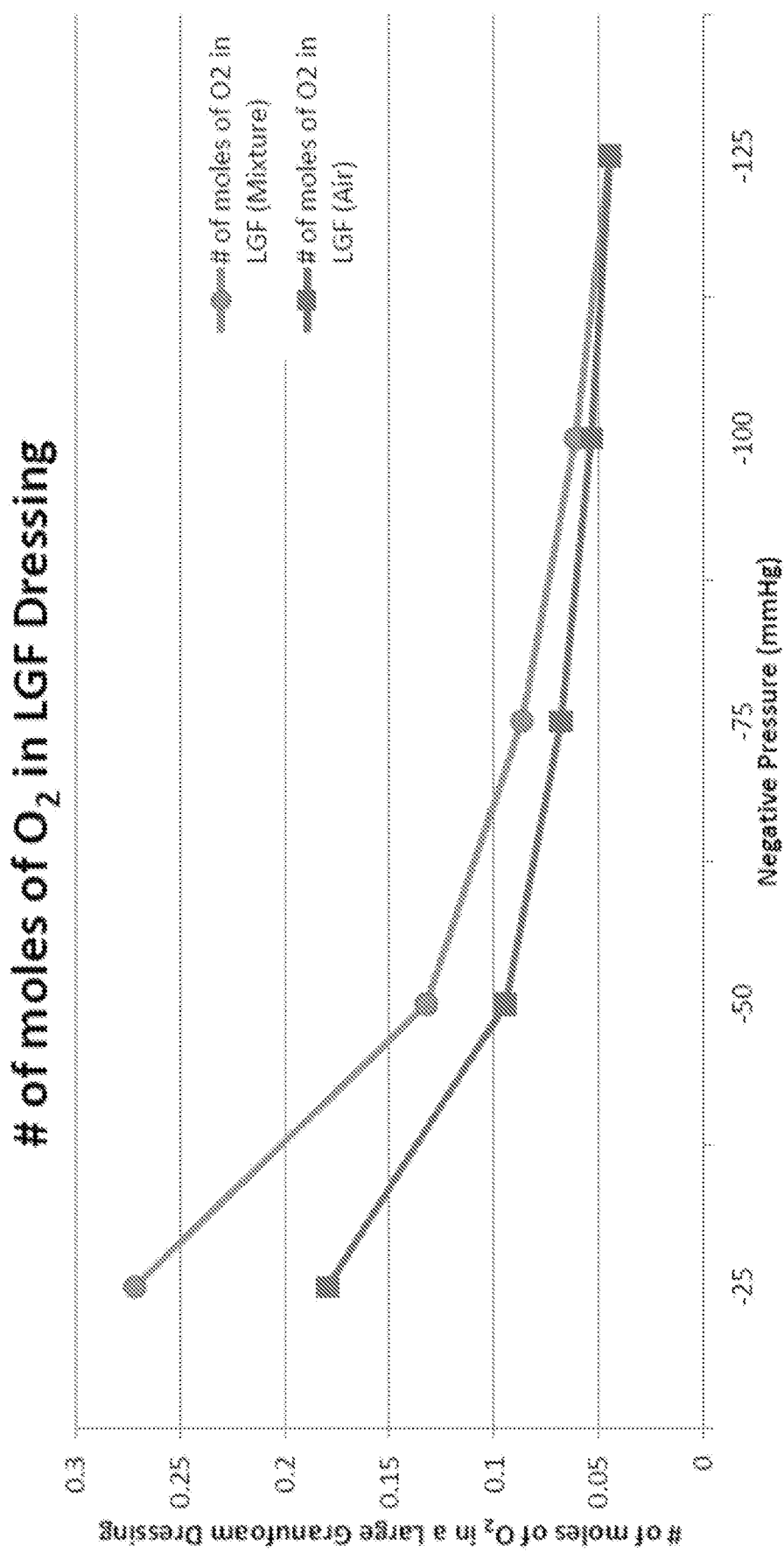

FIG. 10 depicts the change in moles of oxygen in the tested Granufoam Dressing based on the induction of negative pressure.

Figure 11:
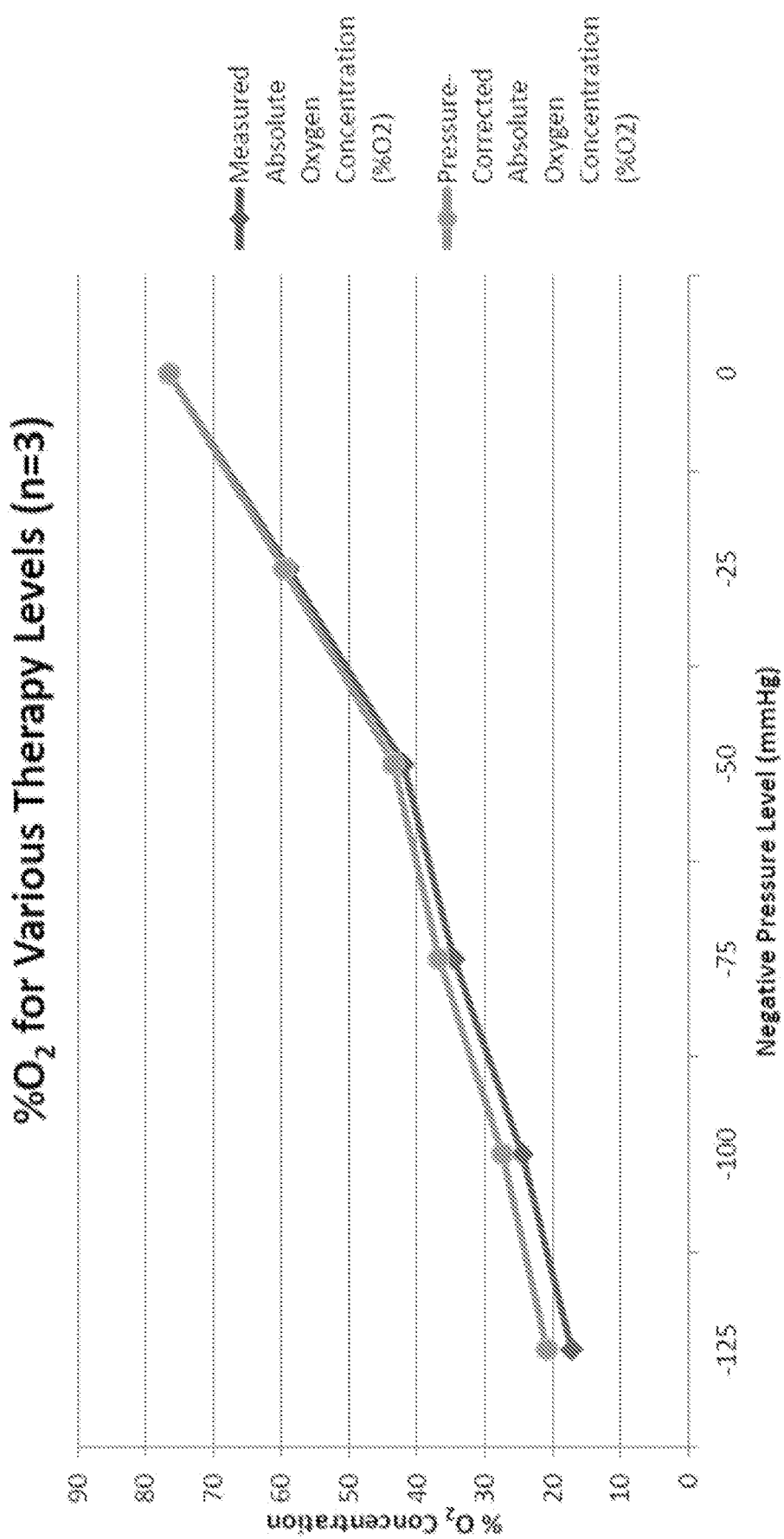

FIG. 11 depicts the change in oxygen purity as negative pressure within the interior volume (e.g., 78) of the dressing is reduced. Here, oxygen was pressurized to 110 bar when introduced into the interior volume (e.g., 78) of the dressing.

Figure 12:
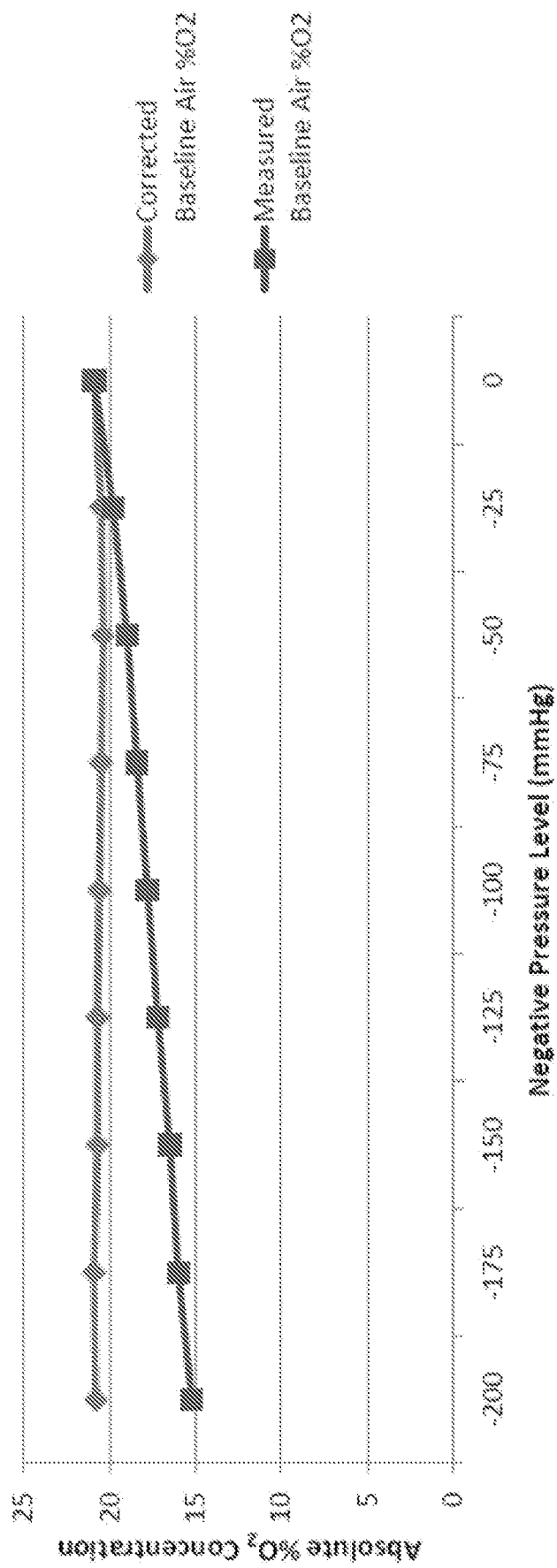

FIG. 12 depicts how sensors (e.g., 86a) are affected by the application of negative pressure within interior volume (e.g., 78) of the dressing. As shown, the target negative pressure range was between −200 mmHg and 0 mmHg. As shown, negative pressure changes reduced the absolute oxygen concentration or the number of oxygen molecules per unit of a volume.

The above specification and examples provide a complete description of the structure and use of illustrative embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the methods and systems are not intended to be limited to the particular forms disclosed. Rather, they include all modifications and alternatives falling within the scope of the claims, and embodiments other than the one shown may include some or all of the features of the depicted embodiment. For example, elements may be omitted or combined as a unitary structure, and/or connections may be substituted. Further, where appropriate, aspects of any of the examples described above may be combined with aspects of any of the other examples described to form further examples having comparable or different properties and/or functions, and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A dressing for facilitating delivery of oxygen and application of negative pressure to target tissue, the dressing comprising:
   a patient-interface layer configured to be in contact with the target tissue;
   a liquid control layer configured to be disposed adjacent to the patient-interface layer and further configured to restrict communication of exudate toward the target tissue;

a manifold that defines a plurality of gas passageways and is configured to allow communication of oxygen to the target tissue;

an oxygen-generating assembly comprising:
  a container including a sidewall that defines a chamber, at least a portion of the sidewall being gas-occlusive; and
  an oxygen-generating material disposed within the chamber and configured to release oxygen when exposed to water; and a gas-occlusive layer configured to be disposed over the manifold and the oxygen-generating assembly and coupled to tissue surrounding the target tissue such that: an interior volume containing the manifold and the oxygen-generating assembly is defined between the gas-occlusive layer and the target tissue; and the gas-occlusive layer limits escape of oxygen from the interior volume between the gas-occlusive layer and the tissue surrounding the target tissue;

wherein the oxygen-generating assembly includes one or more valves configured to permit fluid communication between the chamber and the interior volume.

2. The dressing of claim 1, wherein the oxygen-generating assembly comprises a water —sorbent material and/or a carbon dioxide-sorbent material disposed within the chamber.

3. The dressing of claim 1, comprising one or more valves in fluid communication between the chamber and the interior volume, at least one of the one or more valves is movable between:
  a first position; and
  a second position in which fluid communication between the chamber and the interior volume through the valve is more restricted than when the valve is in the first position.

4. The dressing of claim 3, wherein at least one of the one or more valves is configured to move toward:
  the second position if pressure within the interior volume meets or falls below a threshold pressure; and
  the first position if pressure within the chamber meets or rises above the threshold pressure or at least a threshold value above the threshold pressure.

5. The dressing of claim 4, comprising:
  a controller configured to move at least one of the one or more valves between the first and second positions; and
  one or more sensors configured to capture data indicative of pressure within the interior volume;
  wherein the controller is configured to move at least one of the one or more valves between the first and second positions based, at least in part, on data captured by the one or more sensors.

6. The dressing of claim 5, comprising a negative pressure source configured to be in fluid communication with the interior volume, wherein the controller is configured to control the negative pressure source based, at least in part, on data captured by the one or more sensors.

7. The dressing of claim 6, wherein the controller is configured to deactivate the negative pressure source if pressure within the interior volume, as indicated by data captured by at least one of the one or more sensors, meets or falls below the threshold pressure.

8. The dressing of claim 6, wherein the controller is configured to activate the negative pressure source to reduce pressure within the interior volume if pressure within the interior volume, as indicated by data captured by at least one of the one or more sensors, meets or rises above a threshold pressure.

9. The dressing of claim 5, wherein the controller is configured to move at least one of the one or more valves toward the second position upon or after activation of the negative pressure source.

10. The dressing claim 5, wherein the controller is configured to move at least one of the one or more valves toward the first position upon or after deactivation of the negative pressure source.

11. A method for delivering oxygen and applying negative pressure to target tissue, the method comprising:
  coupling a dressing to the target tissue, the dressing comprising;
    a patient-interface layer configured to be in contact with the target tissue;
    a liquid control layer configured to be disposed adjacent to the patient-interface layer and further configured to restrict communication of exudate toward the target tissue;
    a manifold that defines a plurality of gas passageways, an oxygen-generating material that is configured to release oxygen when exposed to water, and
    a gas-occlusive layer to a patient's tissue such that the gas-occlusive layer is disposed over the manifold and is coupled to tissue surrounding the target tissue such that:
      an interior volume is defined between the gas-occlusive layer and the target tissue; and
    the gas-occlusive layer limits escape of oxygen from the interior volume between the gas-occlusive layer and the tissue surrounding the target tissue; and
    an oxygen-generating assembly configured to be disposed within the interior volume, the oxygen-generating assembly comprising:
      a container including a sidewall that defines a chamber, at least a portion of the sidewall being gas-occlusive; and
      an oxygen-generating material disposed within the chamber and configured to release oxygen when exposed to water, and
    one or more valves in fluid communication between the chamber and the interior volume, at least one of the one or more valves movable between:
      a first position; and
      a second position in which fluid communication between the chamber and the interior volume through the valve is more restricted than when the valve is in the first position; and
  reducing pressure within the interior volume.

12. The method of claim 11, wherein reducing pressure within the interior volume is performed using a negative pressure source that is in fluid communication with the interior volume.

13. The method of claim 11, moving the at least one of the one or more valves toward the first position if pressure within the chamber meets or rises above a threshold pressure.

14. The method of claim 11, moving the at least one of the one or more valves toward the second position if pressure within the interior volume meets or falls below a threshold pressure.

15. The method of claim 11, wherein the dressing comprises one or more sensors configured to capture data indicative of pressure within the interior volume and movement of the at least one of the one or more valves between the first and second position is based, at least in part, on data captured by the one or more sensors.

16. The method of claim 15, wherein the dressing comprises a controller configured to move the at least one of the one or more valves between the first and second positions based, at least in part, on data captured by the one or more sensors.

17. The method of claim 15, wherein:
reducing pressure within the interior volume is performed using a negative pressure source that is in fluid communication with the interior volume; and
controlling the negative pressure source based, at least in part, on data captured by the one or more sensors.

18. The method of claim 17, actuating the negative pressure source to reduce the negative pressure within the interior volume if pressure within the interior volume, as indicated by data captured by at least one of the one or more sensors, meets or falls below a threshold pressure.

19. The method of claim 17, actuating the negative pressure source to increase the negative pressure within the interior volume if pressure within the interior volume, as indicated by data captured by at least one of the one or more sensors, meets or rises above a threshold pressure.

20. The dressing of claim 1, comprising a negative pressure source configured to be in fluid communication with the interior volume.

\* \* \* \* \*